(12) United States Patent
Bahramian et al.

(10) Patent No.: US 6,939,712 B1
(45) Date of Patent: Sep. 6, 2005

(54) MUTING GENE ACTIVITY USING A TRANSGENIC NUCLEIC ACID

(75) Inventors: Mohammad B. Bahramian, Branford, CT (US); Helmut Zarbl, Snoqualmie, WA (US)

(73) Assignee: Impedagen, LLC, Seattle, WA (US)

( * ) Notice: Subject to any disclaimer, the term of this patent is extended or adjusted under 35 U.S.C. 154(b) by 0 days.

(21) Appl. No.: 09/472,558

(22) Filed: Dec. 27, 1999

Related U.S. Application Data
(60) Provisional application No. 60/114,107, filed on Dec. 29, 1998.

(51) Int. Cl.[7] .......................... C12N 15/87; C12N 5/02; C12N 15/12

(52) U.S. Cl. ...................... 435/463; 435/450; 435/325; 435/375

(58) Field of Search ................................. 435/450, 463, 435/325, 375, 455; 800/13, 18, 25; 536/23.1

(56) References Cited

U.S. PATENT DOCUMENTS

| | | | |
|---|---|---|---|
| 5,908,960 A | 6/1999 | Newlander | |
| 6,506,559 B1 * | 1/2003 | Fire et al. | 435/6 |
| 6,531,647 B1 * | 3/2003 | Baulcombe et al. | 800/278 |

FOREIGN PATENT DOCUMENTS

| | | | |
|---|---|---|---|
| WO | WO 94/11494 A1 * | 5/1994 | C12N/5/16 |
| WO | WO 97/01560 | 1/1997 | C07D/487/04 |

OTHER PUBLICATIONS

Gambarotta et.al.; Ets up–regulates MET transcription, 1996, Oncogene 13: 1911–1917.*
Guinaraes et.al., Identification of a novel selD homolog from Eukaryotes, Bactena and Archaea: Is there an autoregulatory mechanism in selenocysteine metabolism? 1996, Proc. Natl. Acad. Sci., vol. 93 15086–15091.*
Dietrich et.al.; Delivery of antigen–encoding plasmid DNA into the cytosol of macrophages by attenuated suicide Listeria monocytogenes, 1998, Nature Biotechnology, vol. 16: 181–185.*
Grillot–Courvain et.al.; Functional gene transfer from inrracellular bacteria to mammalian cells, 1998. Nature Biotechnology, vol. 16:862–866.*
Moreadith et al, 1997, J. Mol. Med., 75: 208–216.*
Seamark et al, 1994, Reprod. Fert. Dev., 6: 653–657.*
Mullins et al, 1996, J. Clin. Invest., 98(11): S37–S40.*
Anderson et al, 1998, Nature, 392(supp): 25–30.*
Verma et al, 1997, Nature, 389: 239–242.*
Capecchi et al, 1994, Scientific American, Mar.: 52–59.*
Soberon et al. *Construction and Characterization of New Cloning Vehicles IV. Deletion Derivatives of pBR322 and pBR325* Gene 9:287–305 (1980).

Calton et al. *Chapter 30—Product Recovery* Manual of Industrial Microbiology and Biotechnology 436–445 (1986) Ed. A. Dimain.
Chomczynski et al. *Single–Step Method of RNA Isolation by Acid Guanidinium Thiocyanate–Phenol–Chloroform Extraction* Analytical Biochemistry 162:156–159 (1987).
Schnieke et al. *Introduction of the human proα1(I) collagen gene into proα1(1)–deficient Mov–13 mouse cells leads to formation of functional mouse–human hybrid type I collagen* Proc. Nat. Acad. Sci. USA 84:764–768 (Feb. 1987).
Sitrin et al. *Developments in Industrial Microbiology* Journal of Industrial Microbiology 27/1:65–75 (1987).
Zarbl et al. *Revertants of v–fos–Transformed Fibroblasts Have Mutations in Cellular Genes Essential for Transformation by Other Oncogenes* Cell 51:357–369 (Nov. 6, 1987).
Bornstein et al. *The First Intron of the α1(I) Collagen Gene Contains Several Transcriptional Regulatory Elements* The Journal of Biological Chemistry 263/4:1603–1606 (Feb. 5, 1998).
Brenner et al. *Analysis of the collagen α1(I) promoter* Nucleic Acids Research 17/15:6055–6064 (Jul. 5, 1989).
Lichtler et al. *Isolation and Characterization of the Rat α1(I) Collagen Promoter* The Journal of Biological Chemistry 264/6:3072–3077 (Feb. 25, 1989).
Rippe et al. *Regulatory Elements in the 5'–Flanking Region and the First Intron Contribute to Transcriptional Control of the Mouse Alpha 1 Type I Collagen Gene* Molecular and Cellular Biology 9/5:2224–2227 (May 1989).
Stacy et al. *Perinatal lethal osteogenesis imperfecta in transgenic mice bearing an engineered mutant pro–α1(I) collagen gene* Nature 332:131–136 (Mar. 10, 1988).
Currie *Regulation of kappa immunoglobulin gene transcription in vitro* Nucleic Acids Research 18/10:2987–2992 (Apr. 9, 1990).
Hoemann et al. *Use of Revertant Cell Lines to Identify Targets of v–fox Transformation–specific Alterations in Gene Expression* Call Growth & Differentiation 1:581–590 (Dec. 1990).

(Continued)

Primary Examiner—Ram R. Shukla
(74) Attorney, Agent, or Firm—Peter J. Knudsen

(57) ABSTRACT

The invention provides compositions and methods for muting expression of an endogenous gene in an animal cell, the muting resulting from providing a transgene to a cell. Expression of which transgene is undetectable. The transgene comprises the muting nucleic acid, which is substantially homologous to a portion of the endogenous gene. The portion of the endogenous gene provided on the transgene can be from the 5'-untranscribed end, from the 3' untranscribed end, from an exon or an intron in the coding portion, or from a portion that overlaps any of these portions. Methods are provided for obtaining muting nucleic acid, and for screening for molecules that can mute the gene, and for molecules that can alleviate muting of the gene.

5 Claims, 9 Drawing Sheets

OTHER PUBLICATIONS

LeFranc et al. *Regulation of the immunoglobulin gene transcription* Biochimie 72:7–17 (1990).

Barker et al. *Retrovirus–Induced Insertional Mutagenesis: Mechanism of Collagen Mutation in Mov13 Mice* Molecular and Cellular Biology 11/10:5154–5163 (Oct. 1991).

Chan et al. *Retrovirus–Induced Interference with Collagen I Gene Expression in Mov13 Fibroblasts is Maintained in the Absence of DNA Methylation* Molecular and Cellular Biology 11/1:47–54 (Jan. 1991).

Dhawan et al. *Cell Adhesion Regulates Pro–α1(I) Collagen mRNA Stability and Transcription in Mouse Fibroblasts* The Journal of Biological Chemistry 266/13:8470–8475 (May 5, 1991).

Ritzenthaler et al. *Transforming–growth–factor–β activation elements in the distal promoter regions of the rat α1 type I collagen gene* Biochemistry Journal 280:157–162 (Jun. 11, 1991).

Staudt et al. *Immunoglobulin Gene Transcription* Annual Review of Immunology 9:373–398 (1991).

Wang et al. *Positive and Negative Regulation of Immunoglobulin Gene Expression by a Novel B–Cell–Specific Enhancer Element* Molecular and Cellular Biology 11/1:75–83 (Jan. 1991).

Kho et al. *Fte–1, a v–fos transformation effector gene, encodes the mammalian homologue of a yeast gene involved in protein import into mitochondria* Proc. Nat. Acad. Sci. USA 89:2200–2204 (Mar. 1992).

Slack et al. *Regulation of Collagen I Gene Expression by ras* Molecular and Cellular Biology 12/10:4714–4723 (Oct. 1992).

Capecchi *Targeted Gene Replacement* Scientific American 52–59 (Mar. 1994).

Bahramian et al. *Direct Gene Quantitation by PCR Reveals Differential Accumulation of Ectopic Enzyme in Rat–1 Cells, v–fos Transformants, and Revertants* PCR Methods and Applications 4:145–153 (1994).

Ingelbrecht et al. *Posttranscriptional silencing of reporter transgenes in tobacco correlates with DNA methylation* Proc. Nat. Acad. Sci. USA 91:10502–10506 (Oct. 1994).

Van Amsterdam et al. *Elevated expression of the junB proto–oncogene is essential for v–fos induced transformation of Rat–1 cells* Oncogene 9:2969–2976 (Jun. 15, 1994).

Farrell et al. *Naturally occurring antisense transcripts are present in chick embryo chondrocytes simultaneously with the down–regulation of the alpha 1(I) collagen gene* The Journal of Biological Chemistry 270/7: 3400–3408 (Feb. 17, 1995).

Jorgensen *Cosuppression, Flower Color Patterns, and Metastable Gene Expression States* Science 268:686–691 (May 5, 1995).

Cogoni et al. *Transgene silencing of the α1–I gene in vegetative cells of Neurospora is mediated by a cytoplasmic effector and does not depend on DNA–DNA interactions or DNA methylation* EMBO Journal 15/12:3153–3163 (1996).

Magis et al. *An upstream activator of transcription coordinately increases the level and epigenetic stability of gene expression* Proc. Nat. Acad. Sci. USA 93:13914–13919 (Nov. 1996).

Meyer *Repeat–Induced Gene Silencing: Common Mechanisms in Plants and Fungi* Biological Chemistry 377:87–95 (Feb. 1996).

Tsai et al. *Cell–Type–Specific Regulation of the Human Tumor Necrosis Factor Alpha Gene in B Cells and T Cells by NFATp and ATF–2/JUN* Molecular and Cellular Biology 16/10:5232–5244 (Oct. 1996).

Bingham *Cosuppression Comes to the Animals* Cell 90:385–387 (1997).

Cogoni et al. *Isolation of quelling–defective (qde) mutants impaired in posttranscriptional transgene–induced silencing in Neurospora crassa* Proc. Nat. Acad. Sci. USA 94:10233–10238 (Sep. 1997).

Metzlaff et al. *RNA–Mediated RNA Degradation and Chalcone Synthase A Silencing in Petunia* Cell 88:845–854 (Mar. 21, 1997).

Pal–Bhadra. et al. *Cosuppression in Drosophila: Gene Silencing of Alcohol dehydrogenase by white–Adh Transgenes is Polycomb Dependent* Cell 90:479–490 (Aug. 8, 1997).

Palla et al. *Enhancer blocking activity located near the 3' end of the sea urchin early H2A histone gene* Proc. Nat. Acad. Sci. USA 94:2272–2277 (Mar. 1997).

Rippe et al. *Binding of upstream stimulator factor to an E–box in the 3'–flanking region stimulates α1(I) collagen gene transcription* The Journal of Biological Chemistry 272/3:1753–1760 (Jan. 17, 1997).

Ivanov et al. *Down–regulation of Tumor Necrosis Factor α Expression by Activating Transcription Factor 2 Increases UVC–induced Apoptosis of Late–stage Melanoma cells* The Journal of Biological Chemistry 274/20:14079–14089 (May 14, 1999).

* cited by examiner

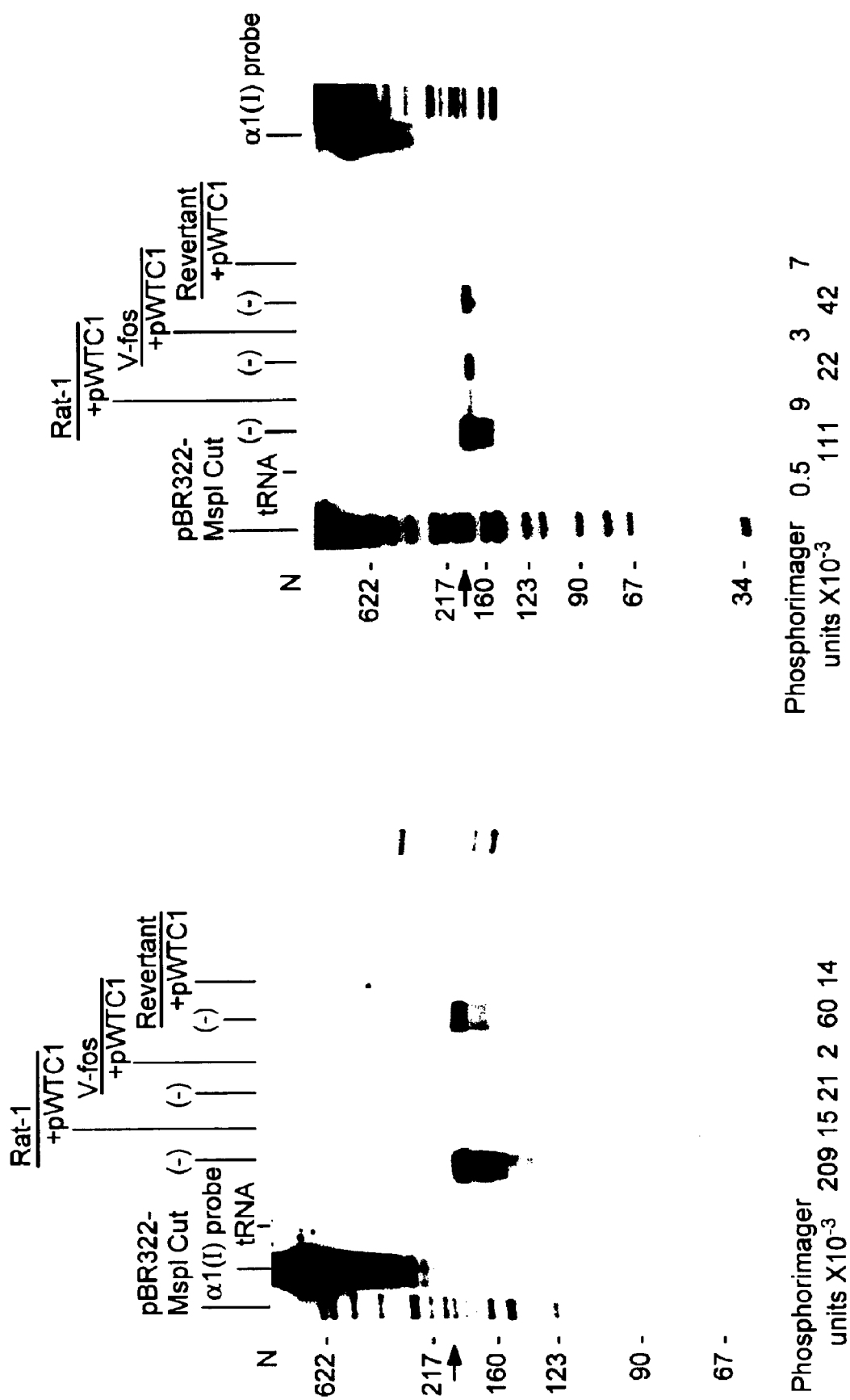

Rat-1/PColCAT0.2
Rat-1        Rat-1/pBR322
GAPDH   
α 1(I)    
Ratio: α1(I)/GAPDH   1.0  0.5  1.0
FIG. 4

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
gtagttcgcc agttaatagt                                          20

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
gctgccataa ccatgagtga                                          20

MUTING GENE ACTIVITY USING A TRANSGENIC NUCLEIC ACID

RELATED APPLICATION

This application claims the benefit of Provisional Application No. 60/114,107, filed in the United States Patent and Trademark Office on Dec. 29, 1998, and which is hereby incorporated by reference herein.

GOVERNMENT FUNDING

This invention was made in part with government support under grants 1RO1-CA50378 awarded by the National Cancer Institute and NIH-2T32-ES07020 toxicology training grant awarded by the National Institute of Environmental Health Science. The government has certain rights in the invention.

FIELD OF THE INVENTION

The present invention relates to muting of a gene in animal cells by a transient homologous transgene or fragment thereof, and more particularly to muting of a selected endogenous gene sequence which can be of genomic or pathogenic origin.

BACKGROUND OF THE INVENTION

Gene silencing or cosuppression by homologous transgenes introduced into the genome of plants has raised considerable interest. A transgene can inactivate the normal (endogenous) gene or another transgene of the same type in different genomic locations via a variety of mechanisms (Baulcombe, D. C. et al., Curr. Opin. Biotech. 7:173–180 (1996)). These phenomena have previously been observed in higher plants (Matzke, M. A. et al., Plant Physiol. 107: 679–685 (1995)), and related processes involved in the silencing of duplicated genes have been observed in fungi (Cogoni, C. et al., EMBO J. 15:3153–3163 (1996); Meyer, P., Biol. Chem. 377: 87–95 (1996)). Cosuppression, a reciprocal function involving interactions between the endogenous gene and the genome-integrated transgene, has been detected in the invertebrate insect *Drosophila* (Pal-Bhadra. M. et al. Cell 90:479–490 (1997)).

In genetically modified plants, transgenes that are stably maintained can be silenced. Transgenes can in addition cause the silencing of the endogenous plant genes if they are sufficiently homologous, a phenomenon known as co-suppression. Silencing occurs transcriptionally and post-transcriptionally but silencing of endogenous genes seems predominantly post-transcriptional (Stam, M. et al., Annals of Botany 79:3–12 (1997)). Various factors seem to play a role, including DNA methylation (Ingelbrecht, I. et al., Proc. Natl. Acad. Sci. USA 91: 10502–10506 (1994)), transgene copy number and the repetitiveness of the transgene insert (Meyer, P., Biol. Chem. 377: 87–95 (1996)), transgene expression level (Vaucheret, H. et al., Plant Cell 9:1495–1504 (1997)), possible production of aberrant RNAs (Metzlaff, M. et al., Cell 88:845–854 (1998)), and ectopic DNA—DNA interactions (Baulcombe, D. C. et al., Curr. Opin. Biotech. 7:173–180 (1996)).

An array of cis-acting DNA elements and trans-acting factors are involved in regulation of expression of pro-collagen genes, including α1(I). DNA transfection experiments have shown that two blocks of both positive and negative regulatory elements, located in the 5'-flanking region and the first intron, contribute to the transcriptional regulation of the pro-α1(I) collagen gene (Brenner, D. A. et al., Nucleic Acids Res. 17:6055–6064 (1989); Rippe, R. A. et al., Mol. Cell. Biol. 9:2224–2227 (1989)). In NIH3T3 mouse fibroblasts, which synthesize large amounts of collagen (2.2% of total protein), about 220 bp of the mouse pro-α1(I) collagen promoter carried on the construct Col-CAT3 (also called pColCAT0.2) showed high transcriptional activity, comparable to that of the highly active SV40 promoter of the pSV2CAT construct. However, constructs carrying increasingly larger 5'-flanking sequences showed reduced amount of the reporter chloramphenicol acetyl transferase gene (CAT) activities of between 65% to less than 20% of that of pCOlCAT0.2 (Rippe, R. A. et al., Mol. Cell. Biol. 9:2224–2227 (1989)). The reporter gene activity being measured in these experiments was a fusion to the pro-α1(I) collagen promoter carried on the transgenic plasmid construct.

The ability to control suppression of gene expression in an animal cell will enable several practical solutions to current problems. For example, reducing expression of an oncogenic transformation effector gene, a drug resistance gene, a radioresistance gene or a viral gene, by employing an appropriate gene delivery system, could provide improved treatment for a variety of cancers and for infections by pathogens, for example, viral infections. Further, determining the effects of suppression of activity of a target gene in a cell would be a useful method for genomic analysis, for example, as a more efficient and rapidly available alternative to engineering a knock-out animal for determining the phenotypes of the cells lacking expression of the target gene. The methods of suppression and the cells thus suppressed can provide screening tools to identify drugs capable of reducing gene expression, and also to identify drugs that can reverse the suppression of gene expression.

SUMMARY OF THE INVENTION

Accordingly, one embodiment of the invention provides a nucleic acid composition for muting expression of a gene with unwanted activity in an animal cell, wherein the muting nucleic acid includes a sequence homologous to an endogenous sequence in the gene, or homologous to a gene of a pathogen. In this embodiment, the gene with unwanted activity is carried on a chromosome. Further, the cell is selected from the group consisting of a cancer cell, an autoimmune cell, a cell of a pathogen, and a cell infected with a pathogen, for example, wherein a cell infected with a virus.

A nucleic acid composition of this embodiment is selected from the group consisting of a DNA, an RNA, and a nucleic acid analog. Further, the nucleic acid analog is selected from the group consisting of a phosphorothioate, a 2'-o-methyl RNA, and a peptide nucleic acid. In an embodiment of the invention, the nucleic acid is double stranded DNA.

An embodiment provides a nucleic acid composition for muting expression of a gene with unwanted activity in an animal cell, wherein the animal is a vertebrate, for example the vertebrate is a warm-blooded animal, and further, wherein the warm-blooded animal is a mammal.

In another embodiment, the invention provides a method for muting expression of an endogenous gene having unwanted activity in a cell of an animal, the method comprising the steps of: (a) providing a muting nucleic acid, and (b) delivering the muting nucleic acid into the cell. According to this embodiment, the step of providing the muting nucleic acid includes providing a nucleic acid composition having a transgene, the transgene having a sequence that is substantially homologous to a sequence of the endogenous gene with unwanted activity. In a further embodiment, the transgene sequence is substantially homologous to an endogenous sequence that is located within a portion of the endogenous gene selected from at least one of the group of: the 5' untranscribed portion, the coding portion including introns, the 3' untranslated portion, the 3' untranscribed portion, and a portion that overlaps the ends of the coding portion of the endogenous gene. The endogenous sequence located in the 5' portion can comprise about 50 to 300 bases in length, or can comprise about 300 to 600 bases in length, can comprise about 600 to 1,000 bases in length, or can comprise about 1,000 to 5,000 bases in length.

In a further embodiment, the invention provides a method wherein the step of delivering the muting nucleic acid in (b) is selected from the group of: transforming, transfecting, electroporating, infecting, and lipofecting the nucleic acid into the cell. For example, delivering the muting nucleic acid can comprise infecting the cell with a genetically attenuated bacterium or virion. A further aspect of the method is that following step (b), the muting nucleic acid is not substantially integrated into a chromosome, for example, the muting nucleic acid is located on a plasmid that is transiently maintained in the cell.

The invention in one embodiment provides a method for identifying a muting nucleic acid that reduces expression of an endogenous target gene having unwanted activity in cells of an animal, comprising the steps of: (a) providing a set of fragments of DNA encoding the target gene, wherein the fragments are engineered into a plurality of vector molecules to produce a recombinant vector library, (b) delivering the vector library into the cells, to form a plurality of transgenic cloned fragment recipients; and (c) comparing expression of the target gene in each of a subset of the cloned recipients, to expression of the target gene in the cells of the animal, to identify a cloned recipient having a vector with the muting nucleic acid, wherein expression of the target gene is reduced. According to this method, the animal is warm-blooded, for example, the animal is a mammal. The vector in one embodiment of the method carries also a chemical resistance gene conferring a phenotype which is ability to grow in the presence of the chemical. A method which is an example of the embodiment can have an additional step of: (a) comparing expression of the resistance gene in the cell having the muting nucleic acid, with expression of the resistance gene in the animal cell, wherein the resistance gene is selected from the group consisting of AMP and CAT, encoding β-lactamase and chloramphenicol acetyl transferase, respectively. A method according to this embodiment can have a further step: (a) comparing expression of a second endogenous gene which is not the target gene in the cell having a muting nucleic acid, with expression of the second endogenous gene in the animal cell, for example the second endogenous gene is GADPH, encoding glyceraldehyde-3-phosphate dehydrogenase.

In another embodiment, a method is provided of evaluating a phenotype of animal cells engineered to mute expression of a target endogenous gene, comprising: (a) transforming animal cells capable of expressing the target gene with the vector having the muting nucleic acid obtained according to a method of above; and (b) observing the transformed cells for an altered phenotype in comparison to the parental animal cells capable of expressing the target gene. Thus the altered phenotype under a set of specified conditions is selected from the group consisting of an alteration of: growth rate, nutritional requirement, contact inhibition among confluent cells, formation of foci, tumorigenicity in nude mice or in a syngeneic rodent strain, presence of a receptor for a ligand, signal transduction in response to an effector molecule, sensitivity to a pathogen, expression of a developmental protein, and cell cycle pattern. The specified conditions different from the conditions for growth of the parental animal cells capable of expressing the target gene comprise at least one of the conditions selected from the group of: an elevated temperature, a depressed temperature, a decreased serum concentration, an elevated serum concentration, a decreased carbon dioxide concentration, an increased carbon dioxide concentration, an increased density of plating, and a decreased density of plating. The animal cells can be present in an embryonic or a postnatal animal.

Yet another embodiment provides a method of screening a plurality of molecules to obtain a composition capable of muting expression of an endogenous gene in cells of a cell line, comprising: mixing a subset of each of the plurality of molecules with a plurality of samples of the cells, to produce a plurality of test cell cultures; providing a nucleic acid capable of muting expression of the gene, transforming the nucleic acid into a sample of the cells, to produce a positive control cell culture having muting of expression of the endogenous gene: and detecting an amount of expression of the endogenous gene in each of the test cell cultures in comparison with the positive control cell culture and with untreated cells of the cell line, such that a test cell culture with substantially reduced expression of the gene compared to expression in the untreated cells, and substantially equivalent expression compared to cells in the positive control culture, identifies the composition capable of muting expression of the gene. An embodiment of this invention provides that detecting expression of the endogenous gene comprises analyzing cell RNA by hybridization with a probe, for example the hybrid of the cell RNA and the probe is digested with RNase, and further, the digested RNA is submitted to gel electrophoresis to determine the size of the cell RNA protected from RNase digestion by the probe.

Another embodiment of the method provides detecting expression of the endogenous gene comprises detecting a color change or absence of a color change in the cells, for example, wherein the color change in the cells is indicative of expression of the endogenous gene which has been fused to a second gene having a colorimetric assay. The molecules can be selected from the group consisting of extracts of natural product fermentations and synthesized organic chemicals, for example, organic chemicals that are synthesized according to combinatorial methods. An embodiment of the invention is a composition obtained by these methods in a pharmaceutically acceptable carrier.

A method of screening a plurality of molecules to obtain a composition capable of alleviating muting of expression of an endogenous gene in cells of a cell line having a muted endogenous gene is provided, comprising: mixing a subset of each of the plurality of molecules with a plurality of samples of the cells having the muted endogenous gene, to produce a plurality of test cell cultures, and detecting amounts of expression of the endogenous gene in each of the test cell cultures in comparison with the cells of the cell line having the muted endogenous gene, and in untreated cells of a parental cell line in which the endogenous gene is not muted, such that a test cell culture with expression of the gene that is substantially greater than the expression in the cell line having the muted endogenous gene, and that is substantially equivalent to expression in cells of the parental non-muted culture, identifies the composition capable of alleviating muting of expression of the gene. A composition identified by this method can be provided in a pharmaceutically acceptable carrier.

In another embodiment, the invention provides a kit for identifying a muting nucleic acid that reduces expression of an endogenous gene, the kit comprising reagents for assaying quantitatively both protection of a riboprobe from ribonuclease digestion, and amount of transfected DNA. A kit provides reagents which comprise chemicals, stabilized enzymes, and buffers. The reagents can comprise diethylpyrocarbonate-treated water, placental RNase inhibitor, tRNA, a buffer containing piperazine-N,N'-bis(2-ethanesulfonic acid), a DNase I digestion buffer, phenylmethylsulfonyl fluoride, and gelatin. The stabilized enzymes can comprise: an RNA polymerase selected from the group of SP6 RNA polymerase and T7 RNA polymerase; a ribonuclease selected from the group of RNase I and a mixture of RNases A and $T_1$; Taq polymerase; proteinase K; and DNase-free pancreatic RNase.

BRIEF DESCRIPTION OF THE DRAWINGS

FIG. 2 shows RNase protection assays for analysis of endogenous pro-α1(I)-collagen mRNA levels in Rat-1, v-fos transformed 1302-4-1, and revertant EMS-1-19 cells, untransfected or transiently transfected with pWTC1. The 850-nt anti sense riboprobes transcribed by T7 RNA polymerase from a mouse pro-α1(I)-collagen fragment (HindIII/EcoRI) of pSTBB0.7 were hybridized with total RNA extracted from equal numbers of cultured cells (about $10^6$), of cells either untransfected or transfected by pWTC1, and harvested at the indicated times after electroporation. In panel (A), cells were harvested and RNA extracted 24 h after electroporation. In panel (B), cells were harvested and RNA extracted 48 h after electroporation.

FIG. 4 shows RNase protection assays that were used to determine the endogenous pro-α1(I)-collagen mRNA levels in Rat-1 cells, untransfected or transiently transfected with either pColCAT0.2 or pBR322. RNase protection assays and determination of the corresponding α1(I)/GAPDH ratio were determined as described in FIG. 3, at 24 hours after transfection.

DETAILED DESCRIPTION OF SPECIFIC EMBODIMENTS

Figure 1:
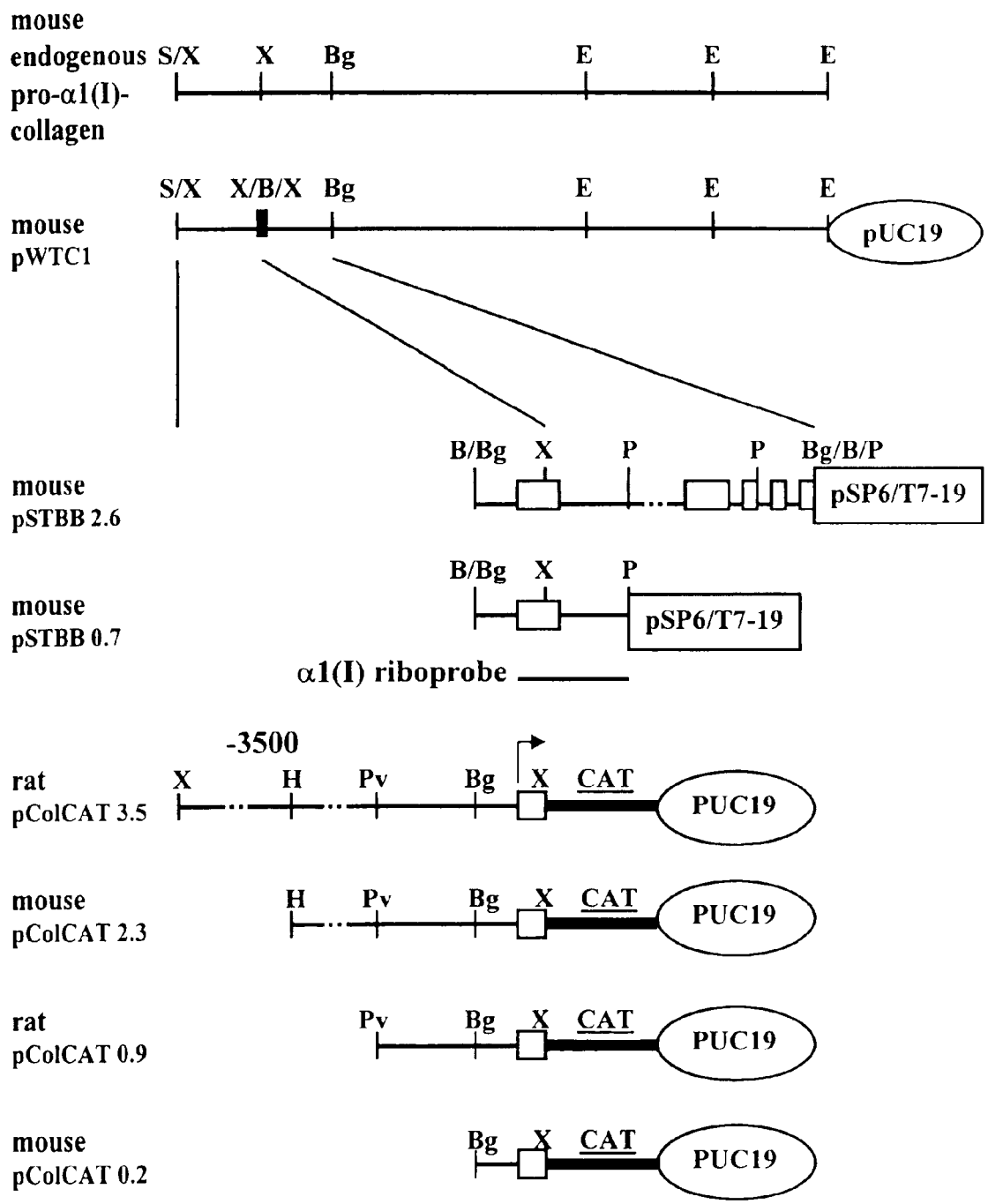
FIG. 1 shows a map of pro-α1(I)-collagen plasmids and the structure of the RNase protection riboprobe. Positions of the first five mRNA exons are indicated by open boxes. The vertical insert marked X/B/X indicates the position of the insertion of the BamHI linker within an XbaI site in the 5' untranslated portion of the mRNA. Horizontal solid or dotted lines represent the procollagen gene sequences. Arrow shows the transcription start position and direction. Relevant restriction sites for the enzymes SalI (S), XbaI (X), HindIII (H), PvuII (Pv), BfgIII (Bg), BamHI (B), PstI (P), and EcoRI (E) are indicated. The position of the pro-α1(I) collagen gene probe transcribed in vitro by T7 RNA polymerase from pSTBB0.7 (EcoRI digested) is shown. This antisense riboprobe of about 850 nucleotides (nt) protects the 194-nt endogenous mouse or rat α1(I) mRNA corresponding to exon 1.

Unless the context otherwise requires, the terms and phrases defined below as well as throughout this description, shall be understood to have the meanings set forth, for purposes of both this description and the following claims.

Homology-dependent gene silencing (also known as quelling and co-suppression) was discovered in plants, fungi, and *Drosophila melanogaster*. These terms refer to the phenomenon of reciprocal silencing among genome-integrated dispersed homologous genes. Mechanisms may have evolved in eukaryotic organisms to inactivate expression of multiple copies of genes, gene overexpression, or abnormal transcription. In fungi and plants, there is evidence that mechanisms involve DNA—DNA association (Matzke, M. et al. Plant Phys. 107:679–685 (1995)) or turnover of RNA (Cogoni, C. et al., Proc.Natl.Acad.Sci.U.S. 94:10233–10238 (1997)).

The genetic regulation observed in embodiments of the invention herein differ from previously described silencing phenomena. The term "muting" means a method of using a transient non-integrated transgene to reduce expression of an endogenous gene, for example located on the genome of a cell, the endogenous gene having a portion of substantial homology to the transgene. Muting of the endogenous gene embodied in the examples herein is independent of expression of the transgene, unlike previously described silencing phenomena.

The term "transgene" means a gene or gene fragment that is or has been exogenously supplied to a recipient cell by any of several procedures known to one of ordinary skill in the art of recombinant DNA methodologies. The recipient cell has been transformed into a transgenic cell. Cells from the same cell line as the recipient cell which have not been engineered to carry the transgene are referred to as "parental" or "untreated" cells. In prior reports describing gene silencing, observations were restricted to cells in which the transgene was integrated into the genome of the recipient cell and stably maintained at one or more sites on one or more chromosomes of the cell.

An "endogenous" gene as used herein generally means a gene or gene fragment that is normally found indigenous to the genome of the organism, and is therefore replicatively maintained by the normal mitotic process of cell division and distributed to gametes by normal meiotic processes. An endogenous gene indigenous to the cell and having unwanted expression can be a gene encoding a protein associated with inflammation, such as a gene encoding TNF-α, for example, or a gene encoding an MHC class II protein associated with an autoimmune disease and expressed in an autoimmune cell. An "autoimmune cell" means an immune cell which has acquired ability to attach an autoantigen.

However in certain embodiments an endogenous gene can mean a gene or gene fragment of a pathogen, such as a virus, bacterium, fungus, protozoan, or helminth, which can be found in a cell or in an animal prior to treatment by introduction of a transgene by a method of the invention herein. An endogenous gene, whether indigenous to the genome or found in a pathogen, is a target for the methods of muting as described herein.

The term "plasmid" means a covalently closed circular DNA molecule. The plasmids of the present invention can replicate in microorganisms but not in animal cells. Therefore the plasmids in transformed recipient animal cells are maintained in the cells into which they have been introduced for a limited number of cell divisions, that is, in a substantially transient condition in the majority of the transformed cells. A plasmid of the invention can be engineered to carry a eukaryotic origin of replication, enabling a greater period of maintenance of the plasmid in the recipient cell.

The term "transformation" means the genetic process of causing a nucleic acid to enter a cell.

The term "transfection" means cellular transformation by a nucleic acid comprising a genetic element from a virus, e.g., the cohesive ends (cos) of bacteriophage lambda, to enter a cell. The transformation of a cell can be achieved by the process of transfection, for example by methods that are chemical in nature (use of calcium phosphate, DEAE-dextran, lipofection by use of liposomes) or physical. The term "electroporation" means a physical process of applying an electric voltage to cells in the presence of a nucleic acid, causing transient pores in the cell membrane such that the nucleic acid enters the cell.

The term "infection" means a biological process of causing a nucleic acid carried on a cell pathogen (such as a virus or a bacterium), to enter a cell. The virus or bacterium can be engineered to deliver a transgene to the recipient cell.

The methods and compositions of various embodiments of the present invention can be used to mute an endogenous gene in an animal cell, for example an oncogene such as ras, or alternatively, can be used to mute a viral gene such as a gene encoding a coat protein from HSV-II or from HIV.

A composition described herein can be administered in an effective dose, in a pharmaceutically effective carrier. The term "effective dose" means that amount of a composition such as a muting nucleic acid, or a drug having a muting effect, or a drug capable of reversing a muting effect, that is provided to achieve a therapeutic end point of altering expression of an endogenous gene in an animal cell. An effective dose can be determined by one of ordinary skill in the pharmacological art.

As used herein, "pharmaceutically acceptable carrier" includes any and all solvents, dispersion media, e.g., human albumin or cross-linked gelatin polypeptides, coatings, antibacterial and antifungal agents, isotonic agents, e.g., sodium chloride or sodium glutamate, and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

Dosage regimens are adjusted to provide the optimum desired response, e.g., a therapeutic response, such as muting of an endogenous gene. For example, a single bolus can be administered, several divided doses can be administered over time or the dose can be proportionally reduced and administered over a time period by infusion, or increased, as indicated by the exigencies of the therapeutic situation.

One of ordinary skill in the medical and pharmacological arts can determine and prescribe the effective amount of the pharmaceutical composition required. For example, one could start doses at levels lower than that required in order to achieve the desired therapeutic effect and gradually increase the dosage until the desired effect is achieved. In general, a suitable daily dose of a composition of the invention will be that amount of the composition which is the lowest dose effective to produce a therapeutic effect. Such an effective dose will generally depend upon the factors described above. It is preferred that administration be intravenous, intracoronary, intramuscular, intraperitoneal, or subcutaneous.

There have been no prior reported phenomena in animal cells of down regulation of gene expression caused by transgenes which had not integrated into at least one site on the chromosomes of a cell's genome. In the transiently transformed cells of the present invention, in which exogenously added genetic material was not generally integrated into the chromosome, the phenomenon of "muting of expression" was observed in several different types of mammalian cells. Muting of expression observed in the embodiments of the present invention was non-reciprocal, i.e., expression of the target endogenous gene was specifically reduced by the presence of the homologous transgene, however the transgene was self-silent or was expressed in a dose-dependent manner. All traces of expression that could be detected in the most highly muted cells were found to have the physical characteristics of the endogenous gene. Muting as the term is here defined has not previously been detected in an animal cell.

Expression of the pWTC1, a plasmid that carries the entire pro-α1(I) collagen gene including 3.7 kb of the 5'-promoter and 4 kb of the 3'-untranslated sequences, was analyzed in transient transfection experiments. This plasmid is marked by the insertion of a linker in the 5'-untranslated region, to enable distinguishing its transcripts from those of the endogenous pro-α1(I) collagen gene (Barker, D. D. et al., Mol. Cell. Biol. 11:5154–5163 (1991)). The ability to distinguish transcripts of the endogenous pro-α1(I) collagen gene from that of the transgene is exploited herein to monitor expression of each of the exogenously supplied transgenic gene and the native endogenous pro-α1(I) collagen gene. This comparison led to the surprising finding that the transgene remains muted in the recipient cells even after several days of growth of cells and dilution of the plasmid number by the cell replication process. Previous pro-α1(I) collagen gene plasmid constructs all were found to express their reporter genes to some extent.

The embodiments of the invention herein are described in examples by which extra-chromosomal pro-α1(I) collagen genes, encoded by exogenous plasmids shown in FIG. 1, greatly reduce the steady-state level of procollagen mRNA transcribed from the endogenous gene, and completely mute the expression of the exogenous transgene. The present examples were conducted in different mammalian cell types, normal (Rat-1 and mouse 3T3) fibroblasts, FBJ v-fos transformed Rat-1 fibroblasts (1302-4-1), and a reventant of v-fos-transformed cells (EMS-1–19). The examples herein show that within hours following cellular transfection by multiple copies of pWTC1, a set of events were found to occur. The endogenous pool of pro-α1(I) collagen mRNA existing prior to transfection was rapidly degraded, and a much-reduced muted steady-state level of RNA was established. The same reduced steady-state level of this mRNA was maintained for several days (up to at least a period of 4 days as shown by examples herein). The transgenes also remained transcriptionally muted (FIGS. 2 and 3). The data in examples herein showed that these events are not stress-related, but are induced by procollagen-specific DNA sequences, and manifest equally well in rat and mouse fibroblast lines (FIGS. 3–6). Evidence for degradation of the endogenous collagen mRNA following transfection by pWTC1 was shown by the observation that within 16 hours post-electroporation, the steady-state level of mRNA for this endogenous gene decreased to less than 10% in Rat-1 and v-fos transformed cells. Considering that the half-life of this mRNA is longer than 8 h, the residual mRNA level 16 hours after transfection would be expected to be no less than 25%, even assuming no new transcription from this gene during the experiment. The steady-state mRNA is comprised of processed cytoplasmic and unprocessed nuclear fractions, and a delay in processing of nuclear RNA could result in its degradation.

The present invention shows that two distinct and adjacent portions of the transgenes (−220 to +115 bp and +115 to +585 bp, with respect to transcription start) contribute to transcriptional muting of the endogenous procollagen gene in normal and v-fos transformed rodent fibroblasts, but not in a revertant of v-fos-transformed Rat-1 cells. Other DNA sequences, from 390 bp past the first exon/intron boundary to the end of exon-5, and from −3500 to −220 bp of the 5'-promoter, do not contribute to muting of this gene. The 3' portion of α1(I) procollagen gene present in pWTC1 carries some additional regulatory elements which effect post-transcriptional muting of the endogenous procollagen gene in all fibroblast lines, including the revertants. The collagen transgenes present in pWTC1 remain transcriptionally muted in all cell lines used in this study. These results indicate that genome integration and activation of this self-silenced gene by cis-acting chromosomal factors, not present in pWTC1, are necessary for its expression. Further examples herein indicate that the muting phenomena are not regulated by synthesis of antisense pro-α1(I) collagen mRNA synthesis complementary to the 5' portion of the gene.

Homologous transgene-induced gene muting has significant potential in gene therapy for viral diseases and for pathological cell proliferative diseases, and for characterization of phenotypes of animal cells lacking expression of a target gene. Developing a transgenic or knock-out animal is an expensive and labor intensive procedure (Sedlack, B. J., Gen. Eng. News 19(19):14 (1999)). Embodiments of the present invention provide methods and compositions for engineering animal cells to mute an endogenous gene, and for evaluating the cells so engineered. In this manner, the functional genomic purpose of knocking out a gene can be evaluated. Further, the effect of muting cells of a tissue or an organ in vivo in a whole animal can likewise be determined, by providing those cells or tissue or organs with a muting nucleic acid for an endogenous gene, and determining the effect on a potential resulting altered phenotype.

Embodiments of the invention provide also methods for screening mixtures of compounds present in extracts of natural products, or arising from organic synthetic methods including combinational methods, to obtain a composition capable of causing muting of an endogenous gene in an animal cell. Similarly, the extracts or the synthesized compounds can be screened to obtain a composition capable of reversing muting of an endogenous gene in an animal cell. Methods of recovery of products from fermentation broths are known to ordinarily skilled artisans of the science of natural products, as described in Carlton. G. J. et al., Ch. 30 in Demain, A. L. et al., "Manual of Industrial Microbiology and Biotechnology," Washington, D.C.; American Society for Microbiology, 1986, p. 436; and in Sitrin, R. D. et al., in "Developments in Industrial Microbiology, Vol. 27," New York; Elsevier Science Publishing Co., 1987, p.65.

Methods of obtaining libraries of compounds are exemplified by U.S. Pat. No. 5,908,960 and the published patent application WO97/01560, which are incorporated by reference herein. Additional enabling patents for construction of particular libraries and methodologies therefor are found in Caldwell, J. W. Biotech. and Bioeng. (Combin. Chem.) 61(1):69–75 (1998).

EXAMPLES

Example 1

Cell Lines, Cell Culture and Transfection

The generation of FBJ v-fos transformed Rat-1 fibroblasts, 1302-4-1, and revertant EMS-1-19 have been described (Zarbl, H. et al., Cell 51:357–369 (1987)). Cell culture medium, and electroporation conditions for transient gene expression have been described (Bahramian, M. B. et al., PCR Methods Applic. 4:145–153 (1994)).

Transfection by DEAE-dextran according to an "extended protocol," was performed as follows: cultured cells were washed twice with phosphate-buffered saline (PBS). DNA (100 µg) was applied in a DEAE-dextran solution to the cells, followed by incubation for 8 h. The DEAE-dextran stock solution is 2 mg/ml dissolved in PBS, filter sterilized and stored at 4° C. A working solution contains 10 ml of DEAE-dextran stock, 10 ml of 1M Tris-Cl, pH 7.3, and 80 ml of serum-free medium, which can be stored and is stable for several weeks at 4° C. To a culture dish of cells was added 34 ml of DNA in the DEAE-dextran working solution, to cover a 10 cm plate. After removing the DNA solution, cells were washed gently twice with PBS, and chloroquine (100 µM in medium+serum) freshly prepared from stock solution (10 mM chloroquine in PBS, filtered and stored in the dark at 4° C.) was applied for 4 h. After removing the chloroquine solution, cells were gently washed twice with PBS, then complete medium with serum was added, and cells were incubated for 48 h.

Example 2

Plasmids and Probes for the pro-α1(I) Collagen Gene

Plasmid pWTC1 (Schnieke, A. et al., Proc. Natl. Acad. Sci. USA 84:764–769 (1987); Slack, J. L. et al., Mol. Cell. Biol. 12: 4714–4723(1992)) contains the entire wild type mouse pro-α1(I) collagen gene, including 3.7 kb of the 5'-flanking promoter portion and 4 kb of the 3'-flanking DNA. This gene has been marked by the insertion of a 21-bp XbaI-BamHI-XbaI linker in the 5'-untranslated portion of the procollagen transcript, which allows the user to distinguish between endogenous and transgene-specific α1(I) mRNAs in an assay of gene expression, for example, by use of a ribonuclease protection assay. Plasmid pSTBB2.6 comprises a 2.6 KBBg/II DNA fragment containing the mouse pro-α1(I) collagen basal promoter, exons 1–5 and introns 1–4, cloned into the BamHI site of pSP6/T7-19 (Gibco/BRL Life Technologies. Inc., Bethesda, Md.). Plasmid pSTBB0.7, used for riboprobe synthesis in RNase protection studies, was derived from pSTBB2.6.

Plasmid pSTBB2.6 was cut by PstI (which cuts at positions +585 of the pro-α1(I) collagen gene in the first intron, at +2067 in the third intron, and in the polylinker), and the 3.5 kb fragment containing the 5'-end of the α1(I) gene plus the vector sequences was isolated and ligated. Digested by EcoRI and transcribed in vitro by T7 RNA polymerase, this plasmid produces an antisense transcript of about 850 nt long, which protect 194 nt of endogenous mouse or rat α1(I) mRNA.

Digestion of pSTBB0.7 with PstI and in vitro transcription by SP6 RNA polymerase, generates sense riboprobes of about 850 nt long, which could potentially protect antisense-α1(I) mRNA of about 600 nt, including the first exon and the 5'-end of the first intron. Plasmids pColCAT3.5 and pCol-CAT0.9 (Lichtler, A. et al., J. Biol. Chem. 264:3072–3077 (1989)) contain respectively 3.6 kb (−3521 to +115) and 1.0 kb (−947 to +115) of the 5'-untranslated portion of rat pro-α1(I) collagen gene fused to the chloramphenicol acetyltransferase (CAT) reporter gene and the simian virus 40 splice and polyadenylation sequences. Plasmids pColCAT2.3 and pColCAT0.2 contain the mouse pro-α1(I) collagen promoters, −2296 to +115 and −220 to +115, respectively (Rippe, R. A. et al., Mol. Cell. Biol. 9:2224–2227 (1989)).

The RNA Century Markers (Cat No. 7780), a mixture of 5 linearized plasmids, were used as templates for in vitro transcription reactions for synthesis of labeled molecular size standards (Ambion, Inc., Austin, Tex.), and the internal standard RNA plasmid, pTR1-GAPDH-mouse (Cat No. 7431), which gives a protected fragment of 316 bp, were purchased from Ambion, Inc. The positive internal control plasmid used in the RNase protection experiments, pLS-1, was constructed by cloning a Klenow-blunted 361-bp XbaI-NcoI fragment from pGAPDH-rat into the SmaI site of pGem 3Z. HindIII-linearized plasmid transcribed by T7 RNA polymerase produced a riboprobe of 473-nucleotides which protected a DNA of 361 bp. Plasmid pGract, a rat β-actin probe in pGem 3Z, carries a 637 bp PCR fragment obtained using primers derived from the human β-actin gene sequence and rat DNA, cloned into the SmaI site. This plasmid was linearized with EcoRI and transcribed by SP6 RNA polymerase in vitro. The antisense riboprobe obtained by this procedure was calculated to be 749 nt, and capable of protecting a 612-nt fragment. This plasmid was linearized also with HindIII and transcribed by T7 RNA polymerase, and the sense riboprobe obtained was used as a negative control in the RNase protection experiments.

Example 3

RNA Purification

Cells were harvested and plasmids were purified and quantitated as described in Bahramian, M. B. et al., PCR Methods Applic. 4:145–153 (1994), which is hereby incorporated by reference herein. A sample having one half of the cells was saved for preparation of DNA from nuclei and determination of transgene copy number by quantitative PCR, while the other half was used for isolation of total RNA (procedure adapted from Chomczynski, P. et al., Anal. Biochem. 162:156–159 (1987)). Since RNA prepared by this method is contaminated with organic chemicals and plasmid DNA, it was further purified as follows. The RNA pellet was dissolved in 50 µl of diethyl pyrocarbonate-treated water (DEPC-water), then precipitated by the addition of 200 µl of 2.5M ammonium acetate and 750 µl of ethanol, and incubated at −20° C. for 1 h. The RNA precipitate was collected by centrifugation at 12,000 g for 5 min at 4° C., redissolved in water and precipitated as above. The RNA pellet was rinsed with 0.5 ml of 75% ethanol/25% 0.1M sodium acetate, pH 5.2, and centrifuged for 2 min at 4° C. The supernatant was decanted, and the RNA pellet was allowed to dry by incubation at room temperature for a few minutes, and was then dissolved in 100 µl of DNase I digestion buffer (40 mM Tris-HCl, pH 7.8, 10 mM NaCl, 6 mM MgCl$_2$, 0.1 mM CaCl$_2$, and 0.1 mM dithiothreitol) containing 100 units of placental ribonuclease inhibitor (RNAguard, Pharmacia LKB) and 1 Kunitz unit of RNase-free DNase I (Boehringer Mannheim Biochemicals, division of Roche Molecular Biochemicals, Indianapolis, Ind.). The sample was incubated at 37° C. for 15 min, and the DNase digestion was stopped by the addition of EDTA solution, pH 8.0, to final concentration of 6 mM.

The sample was extracted once with an equal volume of phenol/chloroform/isoamyl alcohol, and once with chloroform/isoamyl alcohol. The aqueous and organic phases were separated by centrifugation for 5–10 min at room temperature. The aqueous phase was transferred to a fresh tube, and the RNA precipitated from the aqueous phase with 0.3M sodium acetate, pH 5.2, plus 2.5 volumes of ice-old ethanol, and the mixture was incubated on ice for 2 h. The RNA pellet was collected by centrifugation at 12,000 g for 5 min at 4° C., and rinsed with 75% ethanol/25% 0.1M sodium acetate, pH 5.2. The ethanol supernatant was removed completely, and the open tube was left on the bench for a few minutes to allow the remaining to evaporate. The RNA pellet was dissolved in 200 µl of TE (Tris-HCl 10 mM, EDTA 1 mM), pH 7.6, then 500 µl of ethanol was added and the preparation was stored at −70° C. until use.

To recover RNA for ribonuclease protection assay, 2 µl of a 10 mg/ml tRNA solution (type V from wheat germ, Sigma-Aldrich, St. Louis, Mo.; Cat No. R7876) and 22 µl of 3M sodium acetate, pH 5.2, were added to the sample, mixed, incubated at −20° C. for 30 min, and centrifuged at 12,000 g for 5 min at 4° C. The RNA pellet was dissolved in 200 µl of DEPC-treated water; an aliquot of one-fifth of the RNA solution was used for the RNase protection assay. Thus, to the 40 µl aliquot of the RNA solution were added 20 µg of tRNA, 5 µl of 3M sodium acetate, pH 5.2, and 120 µl of ethanol. RNA was precipitated at −20° C. for 30 min, and pelleted by centrifugation at 12,000 g for 5 min at 4° C. The RNA pellet was dissolved in 30 µl of hybridization buffer (40 mM pipes, pH 6.4, 400 mM sodium acetate, pH 7.0, 1 mM EDTA, and 80% deionized formamide) containing $5\times10^5$ CPM of riboprobe.

Example 4

RNase Protection Assay

RNase protection analysis (modified from Bornstein, P. et al., J. Biol. Chem. 263:1603–1606 (1988)) was performed as follows. $^{32}$P-labeled riboprobes were synthesized by in vitro transcription from appropriate plasmids with either SP6 RNA polymerase (Gibco/BRL Life Technologies, Inc., Bethesda, Md.) or T7 RNA polymerase (Promega, Madison, Wis.), respectively, with the manufacturer's reagents, buffers and reaction conditions, in the presence of 50 µCi of $^{32}$P-CTP (DuPont/NEN, Boston, Mass.; 800 Ci/mmol). Labeled riboprobe transcripts were treated for 15 min at 37° C. with RNase-free DNase I (Boehringer-Mannheim Biochemicals), followed by the addition of 20 µg of tRNA and purification of RNA by phenol/chloroform/isoamylalcohol extractions and chromatography on RNase-free G-50 Quick Spin column (Boehringer-Mannheim. Cat. No. 100411). A 0.5 volume of 7.5M ammonium acetate and 2.5 volumes of ethanol were added to the column eluate, mixed, and the mixture was placed at −70° C. for 30 min. The riboprobe was collected by centrifugation for 10 min at 12,000 g at 4° C. The supernatant was removed, and the pellet containing the riboprobe was dissolved in hybridization buffer at $5\times10^5$ CPM/30 µl.

Ribonuclease 1™ (Promega, M4261), the preferred enzyme, was used in the protection experiments according to the manufacturer's instructions. However, in certain experiments designated in the Examples, a mixture of ribonuclease A/T1 (or T1 alone) was substituted for RNase 1 when this enzyme was unavailable. In those occasions, RNase A and T1 (Ambion, Austin, Tex.) were used according to the manufacturers' protocols (Cat No. 1412). Because the RNase A/T1 mixture is not highly specific for single-stranded RNA unlike RNase 1, an internal-control comprising protected RNA was used in each experiment involving RNase A/T1 as a control to assure that the proper extent of digestion was achieved.

Example 5

Quantitative Determination of Transfected DNA and Phosphorimage Analysis

Quantitation of transiently transfected DNA inside the nuclei of cells was achieved by a polymerase chain reaction (PCR) as described previously (Bahramian, M. B. et al., PCR Methods Applic. 4-145-153 (1994)), using a pair of primers (5'-GTAGTTCGCCAGTTAATAGT, SEQ ID NO. 1 and 5'-GCTGCCATAACCATGAGTGA, SEQ ID NO. 2). These primers amplified a specific 223 bp DNA fragment from the β-lactamase gene (Soberon, X. et al., Gene 9:287–305 (1980)).

Radioactivity in each of the $^{32}$P-labeled bands in dried polyacrylamide gels containing the results of RNase protection assays, or in PCR products of transfected DNA, was quantitated by using a Molecular Dynamics Phosphorimager and the computer software (Sunnyvale, Calif.). The ratio of pro-α1(I) collagen major protected bands to an internal standard RNA, transcribed from the rat- or mouse-GAPDH gene (glyceraldehyde-3-phosphate-dehydrogenase), was taken as a measure of gene expression. The GAPDH gene was found to be expressed uniformly in the cell lines herein.

Example 6

Effect of transient Transfection with pWTC1 on Redaction in Steady-State Level of Endogenous pro-α1(I) Collagen mRNA Caused by Transcriptional and Post-Transcriptional Muting, and Muting of Transgenes To enable determination of transgenic pro-α1(I) collagen gene expression in the presence of the endogenous gene expression, mouse riboprobe vector pSTBB0.7 from plasmid pSTBB2.6 was constructed (see FIG. 1). The antisense in vitro transcripts from pSTBB0.7 were found to protect a 194-nt endogenous RNA fragment corresponding to exon-1 of rat pro-α1(I) collagen gene (rat and mouse DNA sequences are highly homologous in this region). However, additional minor protected bands were expected due to the presence of some nucleotide mismatches between rat and mouse DNA. The probe was expected to protect a 118-nt and a 76-nt band from pWTC1, which carries a 21 bp insert in the 5'-untranslated region of the gene.

FIG. 2 shows data from the rat fibroblast lines as indicated, which were each electroporated with 10 µg of pWTC1. After a designated period of cell culture, total RNA was extracted. RNA from equal number of cells in each sample was hybridized to the $^{32}$P-labeled riboprobe, and was subsequently treated with RNase 1 and analyzed on denaturing polyacrylamide gels.

The result of the protection assay for each cell line harvested 24 h post-electroporation is shown in FIG. 2A. Endogenous rat collagen mRNA protected a 194-nt major band (shown by the arrow) and some smaller minor bands of mouse α1(I) probe after treatment with RNase 1. Mouse α1(I)-transcripts from pWTC1 were predicted to protect 118-nt and 76-nt bands. The data from RNase protection experiment are representative of four independent assays with similar results. In three cell lines electroporated with pWTC1 (Rat-1, v-fos transformed and the revertant), the level of endogenous procollagen mRNA was surprisingly greatly reduced. Further, expression of the transgenic procollagen gene as determined by synthesis of mRNA was undetectable.

Muting of the ectopic pWTC1-collagen genes appeared concomitantly with initiation of transcription. Since post-transcriptional processing and stability of the endogenous RNA and the exogenous pWTC1-collagen transgene mRNA were observed previously to be similar in stable tranfectants, and because each transfected cell contains two copies of the endogenous gene and hundreds of copies of the transgene, one of ordinary skill in the art of regulation of gene expression would have expected to detect more transcription of the transgene and less of the endogenous gene. Surprisingly, the contrary is true: pWTC1-collagen mRNA was undetectable even after an extended period of time, and transcripts of the endogenous gene, although greatly reduced in amount, were clearly visible. Therefore, suppression of transcription rather than post-transcriptional mRNA degradation was responsible for the absence of pWTC1-transcripts. In mouse fibroblast cell lines stably transfected with pWTC1 so that the gene was integrated into the cellular genome, the transgenic pro-α1(I) collagen mRNA was expressed distinct from and equivalent to the endogenous α1(I) mRNA (Barker, D. D. et al., Mol. Cell. Biol. 11: 5154–5163 (1991); Chan, H. et al., Mol. Cell. Biol. 11:47–54 (1991); Slack, J. L. et al., Mol. Cell. Biol. 12: 4714–4723(1992); Stacey, A. et al., Nature (London) 332:131–136 (1988)).

Analysis of the contrasting findings of muting of endogenous genes and the non-expressed state of the transient transgenes as shown herein, and those findings reported by others, indicates that integration of pWTC1-collagen transgene into the chromosome was necessary for its expression in those studies.

Example 7

Transcriptional Muting as a Function of Post-Electroporation Time and Comparison to Expression by a Control Endogenous Gene The substantial reduction in the steady-state levels of the endogenous transcripts following transfection by pWTC1 shown herein can be the result of, without being bound by any particular theory or mechanism, increased procollagen mRNA turnover rate, or decreased transcription rate of the endogenous gene, or both. Evidence exists for degradation of the pre-transfection population of the procollagen mRNA shortly after ectopic transfection by pWTC1, and subsequent establishment of a much-reduced steady-state level of this RNA. Several reports have shown that in most systems investigated, pro-α1(I) collagen mRNA is a long-lived molecule with a half-life of >8 h in adherent cells, whether growing, quiescent, or replated (Dhawan, J. et al., J. Biol. Chem. 266:8470–8475 (1991)).

Figure 3A:
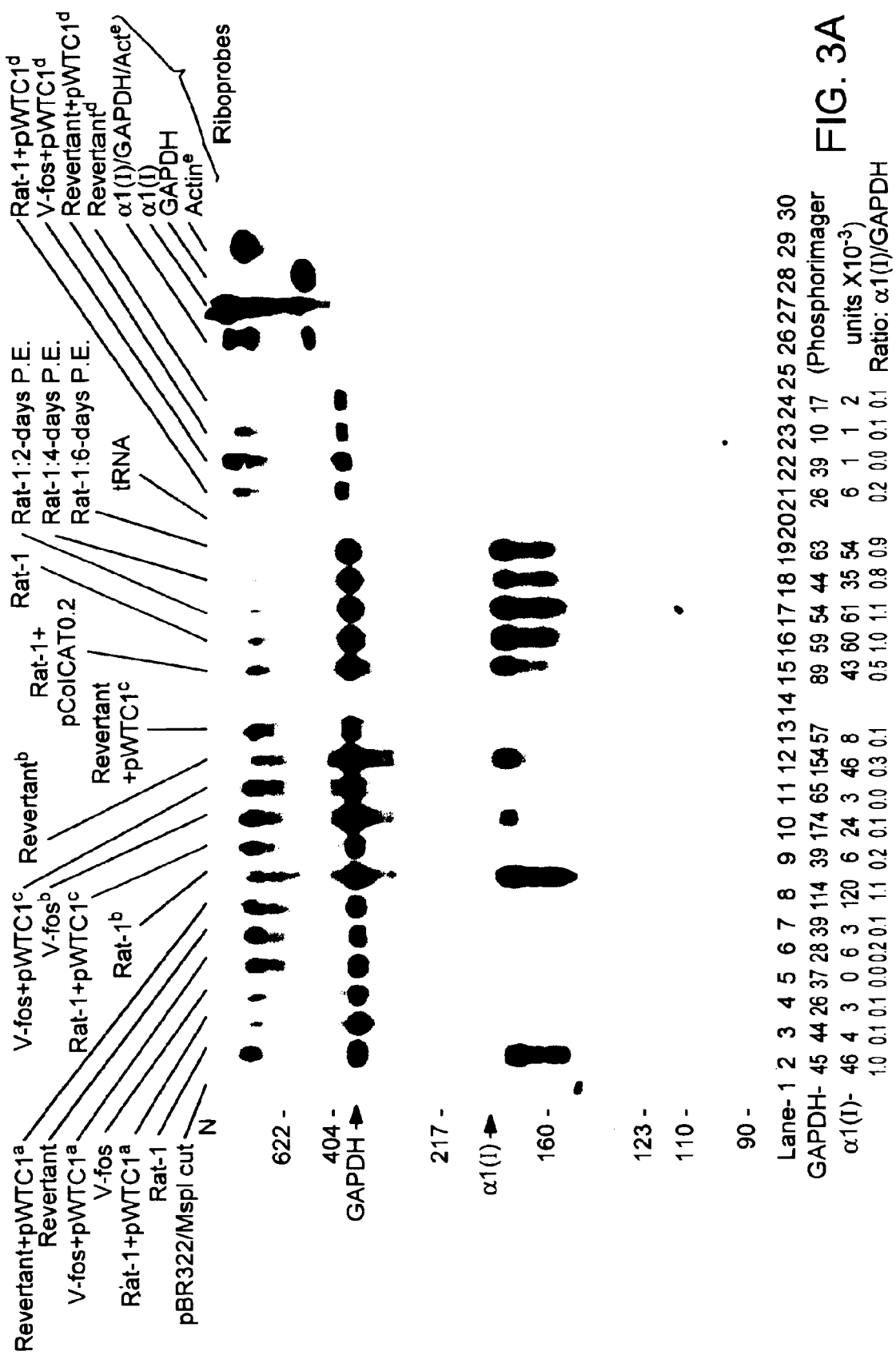
FIG. 3 shows specific suppression of pro-α1(I)-collagen mRNA by transiently transfected α1(I)-collagen genes. Panel (A) is a photograph of RNase protection results using total RNA from Rat-1, v-fos transformed and revertant cells, either transfected with plasmid DNA or not. The α1(I) antisense riboprobe and the expected protected bands are as described in FIG. 2. The 473-nt antisense riboprobe transcribed by T7 RNA polymerase from a rat GAPDH fragment (SmaI/HindIII) of pLS-1 protects a 361-nt GAPDH mRNA fragment which serves as an internal standard. Phosphorimager units determined for each set of GAPDH and α1(I) bands and the corresponding α1(I)/GAPDH ratio are indicated. (a) Cells were harvested 24 h post-electroporation with pWTC1. (b) Cells were electroporated without any DNA 16 h before harvesting. (c) Cells were harvested 48 h post-electroporation with plasmid. (d) DEAE-dextran transfection was used in these samples. Viability of cells after this transfection was less than 20% of that obtained by electroporation, therefore, less RNA was available for use. (e) A rat B-actin sense riboprobe, described in Materials and Methods, was used as a negative internal control (in addition to tRNA) for RNase protection assays. Cells used for RNA preparations 17–19 were harvested at the indicated number of days post-electroporation (P.E.) with no DNA. Panel (B) shows a determination of plasmid β-lactamase gene copy numbers corresponding to the transfected samples in A, using quantitative PCR amplification of a 223 bp fragment of the Amp gene. Lane numbers in A and B are related. (f) Numbers refer to the observed total number of plasmids in the total number of transfected cells ($10^6$–$10^7$ cells per determination).
Figure 3B:
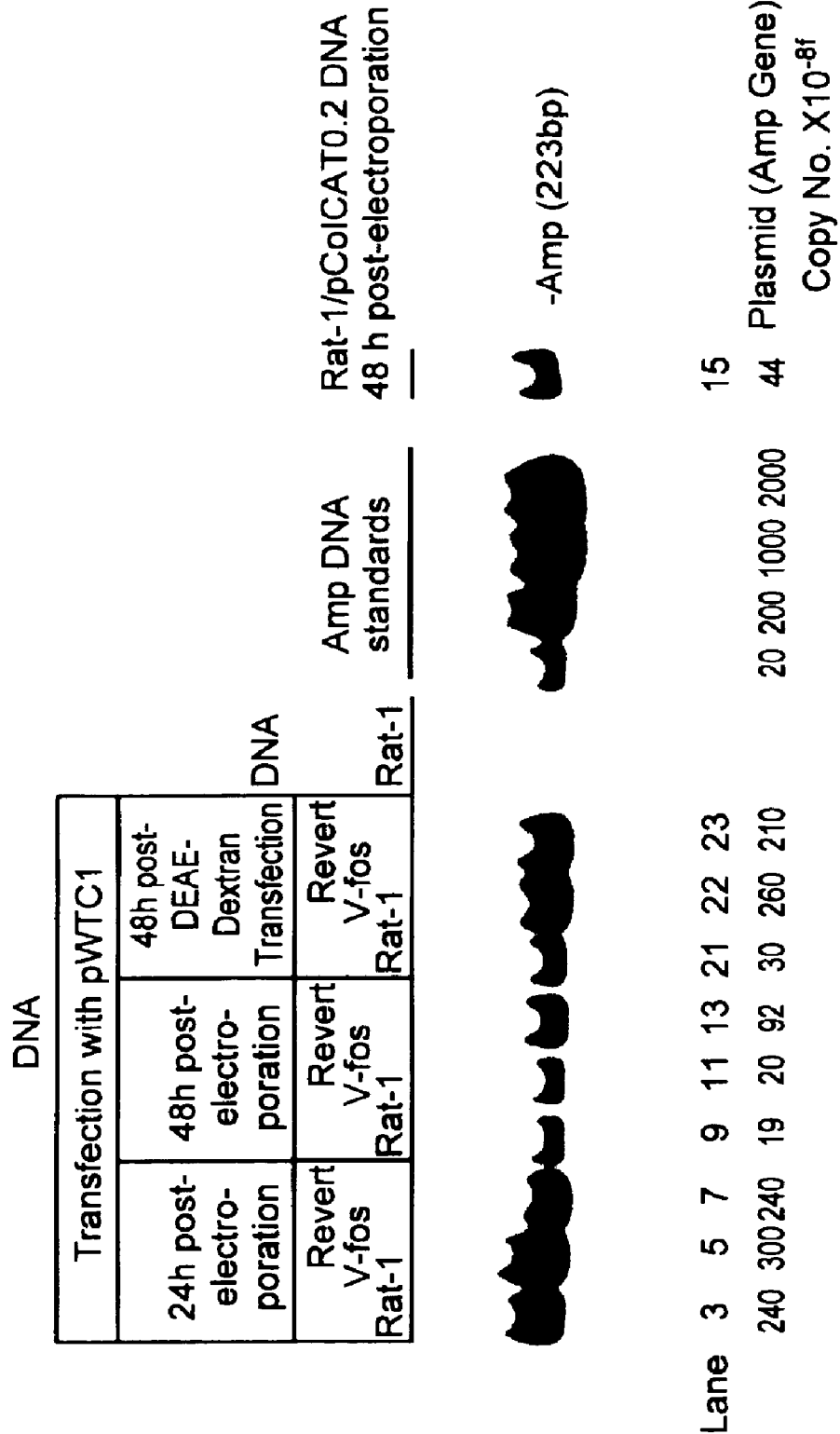

FIG. 2 shows results obtained using RNA prepared only 16 h after electroporation of Rat-1 cells with pWTC1. This result was similar to the result obtained in 24 h post-electroporation cells (FIG. 2A): the level of endogenous collagen mRNA was about 7% that of the control cells. Assuming a half-life for this mRNA of 8 h and that RNA turnover was the sole factor in loss of this species, the residual pro-α1(I) collagen mRNA prepared at a time point of 16 h after electroporation would be expected to be found at a minimum only as low as 25% of the control cells, even in the absence of any de novo transcription. Thus the ene muting observed here was found to be partly due to a post-transcriptional component. The results of a 48 h post-electroporation (FIG. 2B) RNA preparation were also similar to the 24 h point, in spite of ongoing dilution of the transfected DNA by an additional round of cell division. To achieve precise quantitation of data showing relative transcription of an endogenous gene in a cell line from various experiments, and to compare expression among different cell lines, the level of endogenous GAPDH mRNA was determined for each data point. GAPDH was found to be expressed equally in Rat-1, v-fos transformed and revertant cell lines. Thus, GAPDH mRNA could be employed as a reliable internal control for the subsequent ribonuclease protection experiments and for computations of specific pro-a 1(1) collagen gene expression levels. The data shown in FIG. 3 illustrate such data with the ratio of α1(I)collagen/ GAPDH indicated for each lane. This ratio represents the specific expression of the endogenous collagen gene under the designated condition, normalized to the GAPDH internal standard. The specific expression of pro-α1(I) collagen for samples electroporated with pWTC1 followed by cell culture for 24–48 h, was dramatically reduced in all cells electroporated with pWTC1, to a level of less than 10% in Rat-1 and v-fos transformed cells, and to about 30% in the revertant cells (FIG. 3A, lanes 2–13). The average number of transfected plasmids per cell was estimated by PCR. Expression of the GAPDH gene was unaffected in these cells.

Since all of the plasmids carry the P-lactamase gene (Amp), a fragment of the Amp gene was amplified and quantitated by phosphorimaging, to determine the plasmid copy number in each of the recipient cell lines. The data presented in FIG. 3B indicate the number of plasmids in $10^6$–$10^7$ cells harvested (generally, several thousand copies per cell) and show that the extent of gene muting was unaffected by fluctuations in the average plasmid copy number per cell.

The above experiments were repeated also with RNA isolated from cells up to 4 days post-electroporation; the results were essentially similar to those shown here for 16–48 h. These results indicate that, shortly after ectopic transfection of the rat fibroblast cell lines by pWTC1, the endogenous pre-transfection population of procollagen mRNA was degraded, and a much-reduced steady-state level of this mRNA was maintained for at least several days. Absence of the protected RNA bands corresponding to pWTC1-collagen transgenes in the above experiments indicates that the transgenes were not transcribed. Since the endogenous and the transgenic procollagen transcripts have equal stabilities (Slack, J. L. et al., Mol. Cell. Biol. 12:4714–4723(1992)), and there are many more copies of the transgene per cell than the endogenous gene in the transfectant cells, lack of transcription rather than mRNA instability was determined to be the primary basis for the absence of the transgenic pWTC1-collagen transcripts.

Example 8

Transgene-Induced α1(I) Gene Muting and mRNA Instability are not Stress Related

Shock or stress applied to the cells by a process, for example, by electroporation or trypsin-EDTA treatment for suspension of the cells, might induce the observed muting phenomenon. A stress mechanism of gene muting would predict that extending the post-electroporation incubation time to 48 h and longer instead of the 24 h used supra, would provide a greater recovery period and relieve some of the observed suppression. However this result was not obtained (see, for example, FIGS. 2 and 3). Changing the transfection method to a gentler one, such as treatment with DEAE-dextran rather than by electroporation, should, according to this model also reduce the muting, however this result also was not obtained (FIG. 3, lanes 21–24). Further, to examine the effect of this enzymatic and mechanical treatment on the expression of the endogenous collagen gene, control non-electroporated cells in the 48 h experiment (FIG. 3), were trypsinized and replated 16 h prior to harvesting. FIG. 3 lanes 16–19 shows RNase-1 protection assays on RNA samples from equal numbers of cells harvested 2, 4, and 6 days after electroporation in the absence of DNA, respectively, and non-electroporated cells. The results (lanes 8–13) show that trypsin-EDTA treatment did not mute endogenous gene expression.

The data from this experiment show that the shock of electroporation per se did not alter the pattern of gene expression for either the internal standard or for the procollagen gene, since both the absolute values and the ratios of α1(I)/GAPDH mRNA were similar, regardless of cell treatment. These data do not support the hypothesis that specific gene muting is due to cell shock or stress, but rather these data point to a molecular intracellular mechanism.

Example 9

Gene Muting and Transcript Destabilization are Mediated by Specific DNA Sequences The construct pColCAT0.2 contains 220 bp of the pro-α1(I) collagen promoter plus 115 bp of the untranslated portion of exon-1 genetically fused to the CAT gene. This construct has been shown to express the CAT protein efficiently in a number of different cell systems.

In Rat-1 cells transfected with this plasmid, the endogenous procollagen gene was suppressed by 50%, compared to untransfected cells (FIG. 3, compare lanes 15 and 16). However, the transgenic mRNA was not detectable, presumably, because it was rapidly turned over. Transfection of Rat-1 cells by control plasmid pBR322 (carrying only prokaryotic genes), did not alter the level of expression of the endogenous pro-collagen gene (FIG. 4), but pColCAT0.2 and pWTC1 both reduced the steady state levels of this mRNA. These data show that suppression and destabilization of the endogenous procollagen transcripts are mediated by a sequence specific mechanism.

To determine whether negative regulatory sequences in the transgenes would decrease the transcription activity of the endogenous a 1(1) promoter, ribonuclease protection experiments were performed. Following electroporation with various constructs carrying different lengths of rat or mouse α1(I) promoter attached to the CAT gene, the specific expression of the endogenous collagen gene, and the specific expression of the CAT gene in different cell lines were determined. Enzyme immunoassay for the quantitative determination of *Escherichia coli* CAT protein in transfected eukaryotic cells was performed by CAT ELISA (Boehringer-Mannheim, Cat. No. 1363 727), according to the protocols and with the materials provided by the manufacturer.

Figure 5:
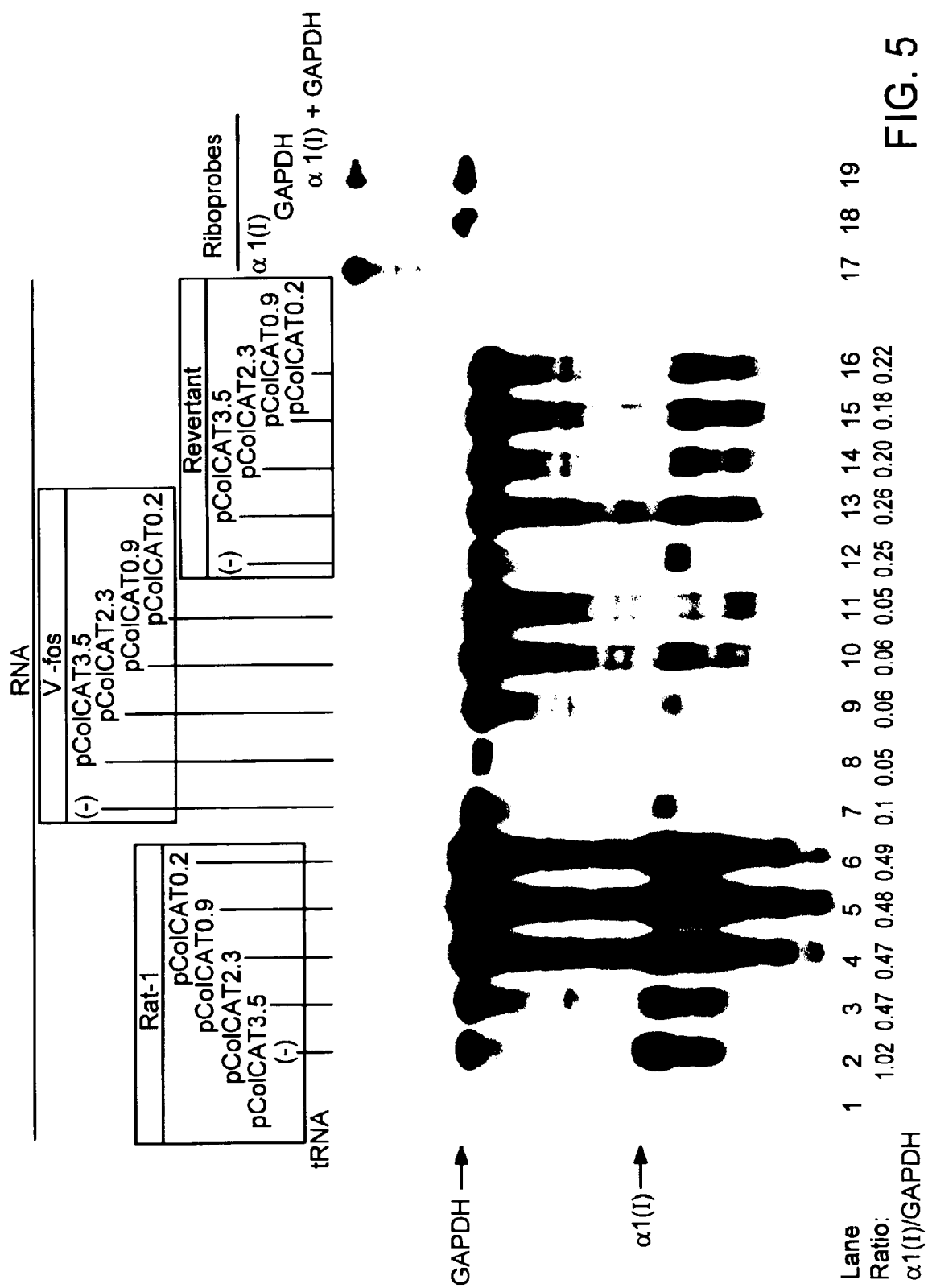
FIG. 5 shows an RNase 1 protection assay-based deletion mapping of the pro-α1(I)-collagen promoter region, to identify collagen mRNA suppressive elements in Rat-1, v-fos transformed 1302-4-1 and revertant EMS-1-19 cells. The α1(I) and GAPDH-rat antisense riboprobes and the expected protected bands are as described in FIGS. 2 and 3. The α1(I)/GAPDH protected-bands ratios, quantitated by phosphorimager, are shown.

Cells carrying each of the four promoter constructs, rat pColCAT3.5, mouse pColCAT2.3, rat pColCAT0.9, and mouse pColCAT0.2 (containing, respectively, 3521, 2296, 947, and 222 bp of the 5'-flanking promoter sequences), were found to produce the same result in the same cell line, compared to untransfected cells of that cell line (FIG. 5). In Rat-1 and v-fos transformed fibroblasts transfected with any of these plasmids, the endogenous collagen mRNA was muted to 50% (FIG. 5, lanes 2–11) compared to the untransfected parent cells. The plasmid bearing a length of sequence including the 222 bp proximal promoter and 115 bp of the beginning of the first exon sequences was sufficient to achieve 50% muting of the endogenous collagen gene transcription, and the promoter sequences upstream of −222 were found not to additionally contribute to the muting of expression. These results showed that there was no relationship between the level of muting of the endogenous gene and the activity of different promoter constructs.

In the revertant EMS-1-19 cell line transfected with each of the various α1(I) promoter constructs, expression of the endogenous procollagen genes was not significantly different from the control, untransfected cells (FIG. 5, lanes 12–16, i.e., no muting was observed). Transfection efficiencies of different constructs into each of the different cell lines were comparable. Taken together, these data show that one or more specific transcription enhancing factors which interact with the procollagen proximal promoter were titrated by the presence of the multiple copies of the exogenous transgenes electroporated into Rat-1 and v-fos-transformed cells, resulting in decreased transcription from the endogenous α1(I) gene.

Revertant cells, expressing endogenous procollagen independent of this factor(s), remained unaffected by transfection with the plasmids carrying different portions of the procollagen promoter. However, the transcription-start-proximal promoter sequences cannot account for all of the endogenous gene muting observed when cells were transfected by pWTC1. This plasmid contains additional procollagen regulatory elements at the 3'-end, which caused additional muting of transcription and/or the mRNA instability in all of the three cell lines. Muting of endogenous procollagen mRNA by the combined 5' and 3' elements present in pWTC1 was 70% for the revertant, and greater than 90% for Rat-1 and v-fos-transformed cells.

These data show that in transient transfection of α1(I)-5'-promoter constructs of various lengths, employing sensitive techniques of ribonuclease protection and quantitative-PCR for determinations of mRNA steady-state level and plasmid copy number in cell nuclei, respectively, the sequences −222 to +115 caused the endogenous gene muting by 50% in Rat-1 and v-fos transformed cells. Further upstream sequences, to −3521, showed no additional muting effect (FIG. 5).

Example 10

Sequences from the Middle of Exon-1 to the Initial Quarter of Intron-1 Contribute to the Endogenous α1(I) Procollagen Gene Muting The construct pSTBB2.6 carries a 2.6 KBBgl II fragment containing transcription-start-proximal 222 bp upstream of the mouse α1(I) promoter, and also exons 1–5 and introns 1–4, cloned into the Bam HI site of the vector pSP6/T7-19 (Gibco-BRL). The plasmid pSTBB0.7 is a deletion construct derived from pSTBB2.6, which contains the promoter, the first exon and the initial 390 bp of the first intron (FIG. 1). These constructs were investigated in Rat-1 and v-fos transformed 1302-4-1 cells for the ability to further suppress the endogenous collagen gene. Both constructs were predicted to express the encoded truncated mRNA poorly, by virtue of two features: they carry the first-intronic sequences which contain sequences that are inhibitory to the transcription, and they are unstable because they lack the 3'-end sequences. Since all of the α1(I) DNA sequences carried by pColCAT0.2 are present in constructs pSTBB2.6 and pSTBB0.7, at minimum 50% suppression of the endogenous α1(I) gene would be predicted following transfection of the cells by either of these constructs. Any additional inhibition would be attributed to the extra exon/intron sequences carried by these constructs.

The results (FIG. 6A) show that there was about 70% reduction of the level of endogenous α1(I) protected bands in Rat-1 or v-fos-transformed cells transfected with either pSTBB2.6 or pSTBB0.7. Since these constructs performed similarly in suppression of the procollagen gene in the protection assays, only the DNA sequences from +115 to +585, and no other sequences to the end of exon-5, contributed to the collagen gene muting.

Figure 6B:
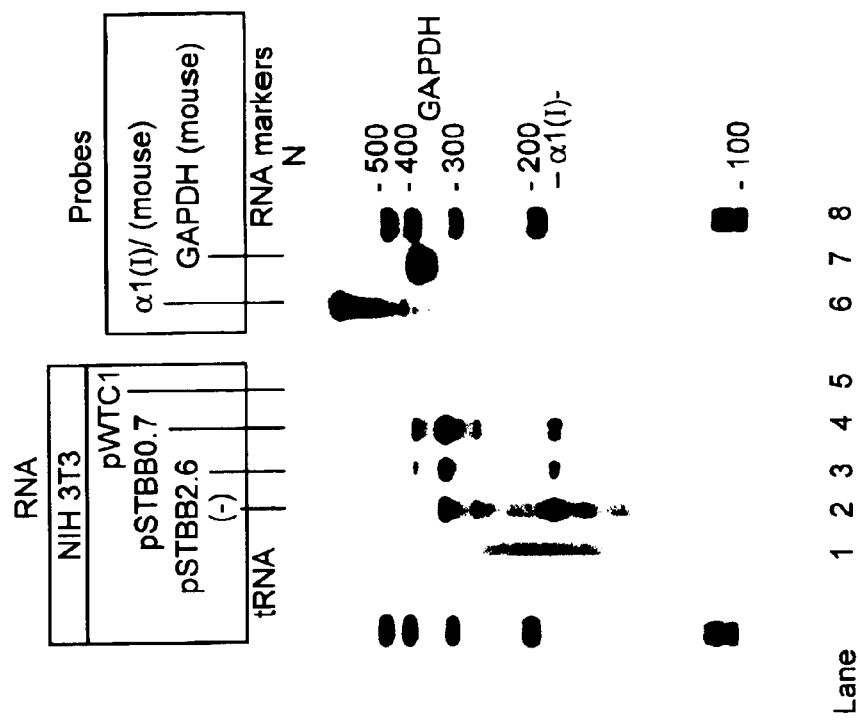
FIG. 6 shows ribonuclease A/T1 protection assay used to identify collagen mRNA suppressive elements in the first five exon/intron regions in various rodent fibroblast cell lines. Panel (A) shows an RNase protection assay using total RNA from Rat-1 and v-fos transformed 1302-4-1 cells untransfected or transiently transfected with either pSTBB2.6 or pSTBB0.7. Panel (B) shows an RNase protection assay using total RNA from mouse NIH 3T3 fibroblasts untransfected or transiently transfected with the plasmids indicated. The α1(I) and GAPDH-rat antisense riboprobes and the expected protected bands are as described in FIGS. 2 and 3. The 406-nt antisense GAPDH-mouse riboprobe transcribed from the pTR1-GAPDH-mouse protects a 316-nt GAPDH-mouse mRNA fragment. Panel (C) shows a determination of the number of copies of various plasmids transfected into different rodent cell lines shown in Panels A and B, using quantitative PCR amplification of the Amp gene and phosphorimager analyses.
Figure 6A:
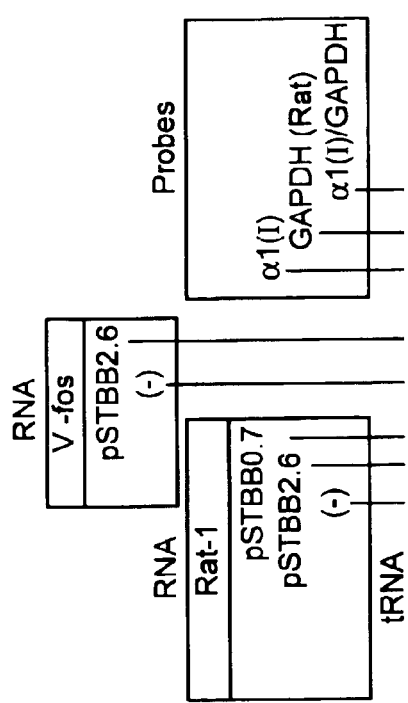
Figure 6C:
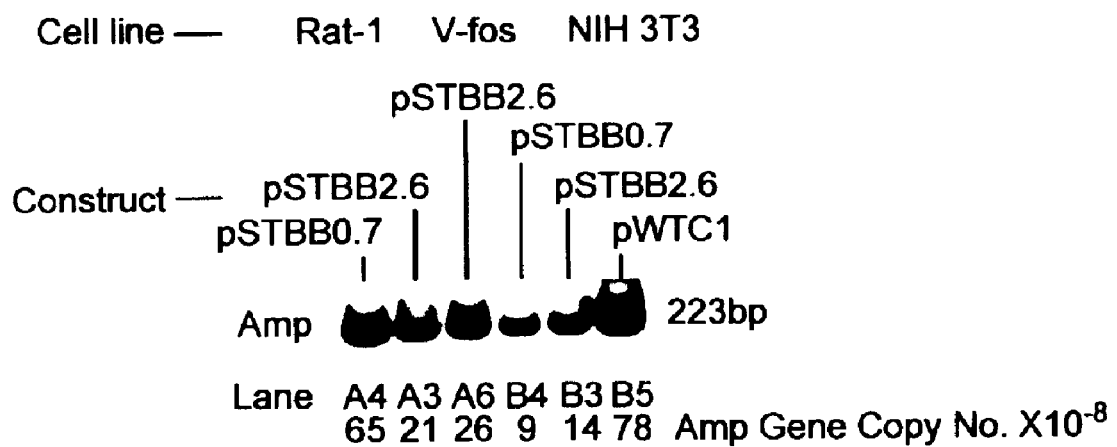

Additional muting was observed with the construct carrying the basal promoter and the initial part of exon 1 (−222 to +115), and further extending to the rest of the exon 1 and 390 nucleotides of the initial portion of intron 1(+116 to +585). The two regions combined resulted in 70% transcriptional muting of the endogenous collagen gene in Rat-1 and v-fos transformed fibroblasts. Further downstream sequences, from +586 to the end of exon 5, did not cause additional decrease of the extent of the endogenous transcripts, therefore do not carry muting elements (FIG. 6A).

Example 11

Muting of the Procollagen Genes in Fibroblasts of Mouse And Rat Origin Occurs to the Same Extent In order to examine whether the endogenous and exogenous collagen gene-muting phenomena were unique to the rat fibroblasts, or were due to transfection of rat cell lines by mouse constructs, mouse NIH3T3 cells were transfected with each of plasmids pSTBB2.6, pSTBB0.7, and pWTC1. The purified RNA samples were analyzed by RNase protection assays, using the mouse α1(I) and the mouse internal standard (GAPDH gene) riboprobes. The results obtained (FIG. 6B) were similar to those observed with rat fibroblasts; about 70% suppression of the endogenous gene by pSTBB2.6 and pSTBB0.7, was observed. A dramatic reduction by pWTC1 was found, although the computation of the specific expression of the latter was complicated by high noise to signal ratio in the corresponding lane. No protected band corresponding to pWTC1-α1(I) procollagen transcripts was detected, even after prolonged film exposures, indicating total transcriptional muting of the exogenous transgenes. Transfection efficiencies of various cells (1–3× $10^6$ cells recovered after transfection) by different constructs were comparable (FIG. 5C).

Example 12

Gene Muting is not Dependent on the Level of Expression of the Transgene

Although muting of the endogenous gene was observed using constructs that carried either the pro29 (I) collagen gene or the CAT reporter gene, each transcript included the 5'-untranslated region of the collagen transcript. If these sequences were involved in muting, the level of the transcripts present in the recipient cells might determine the extent of gene muting. CAT assays were routinely conducted during all transfection experiments, as relatively easy control assay to provide a second level of demonstration of successful transfection of the cells.

The results in Table I are from CAT assays performed on cell extracts from the same transfection experiments shown in FIG. 5. A comparison of these two data sets clearly demonstrates that different promoter constructs with very different rates of gene expression were equally effective at gene muting. While these data indicate that there is no relationship between the rate of expression of the various constructs and the level of the endogenous gene muting, it is not possible to rule out that a low undetectable level of transgene expression is required for muting.

Example 13

Pro-α1(I) Collagen Gene Muting is not Regulated by Differential Antisense mRNA Synthesis Complementary to the Initial 585 bp of the Gene Down-regulation of the α1(I) collagen gene in chick embryo chondrocytes is accompanied by the presence of large antisense transcripts of moderate stability that span both ends of the gene (Farrell. C. M. et al., J. Biol. Chem. 270: 3400–3408 (1995)). To investigate possible involvement of antisense RNA in regulation of the rat fibroblast pro-α1(I) collagen gene, and differential antisense RNA synthesis in the procollagen gene muting phenomena, RNA obtained from the untransfected and transfected cell lines was analyzed by RNase protection experiments.

Figure 7:
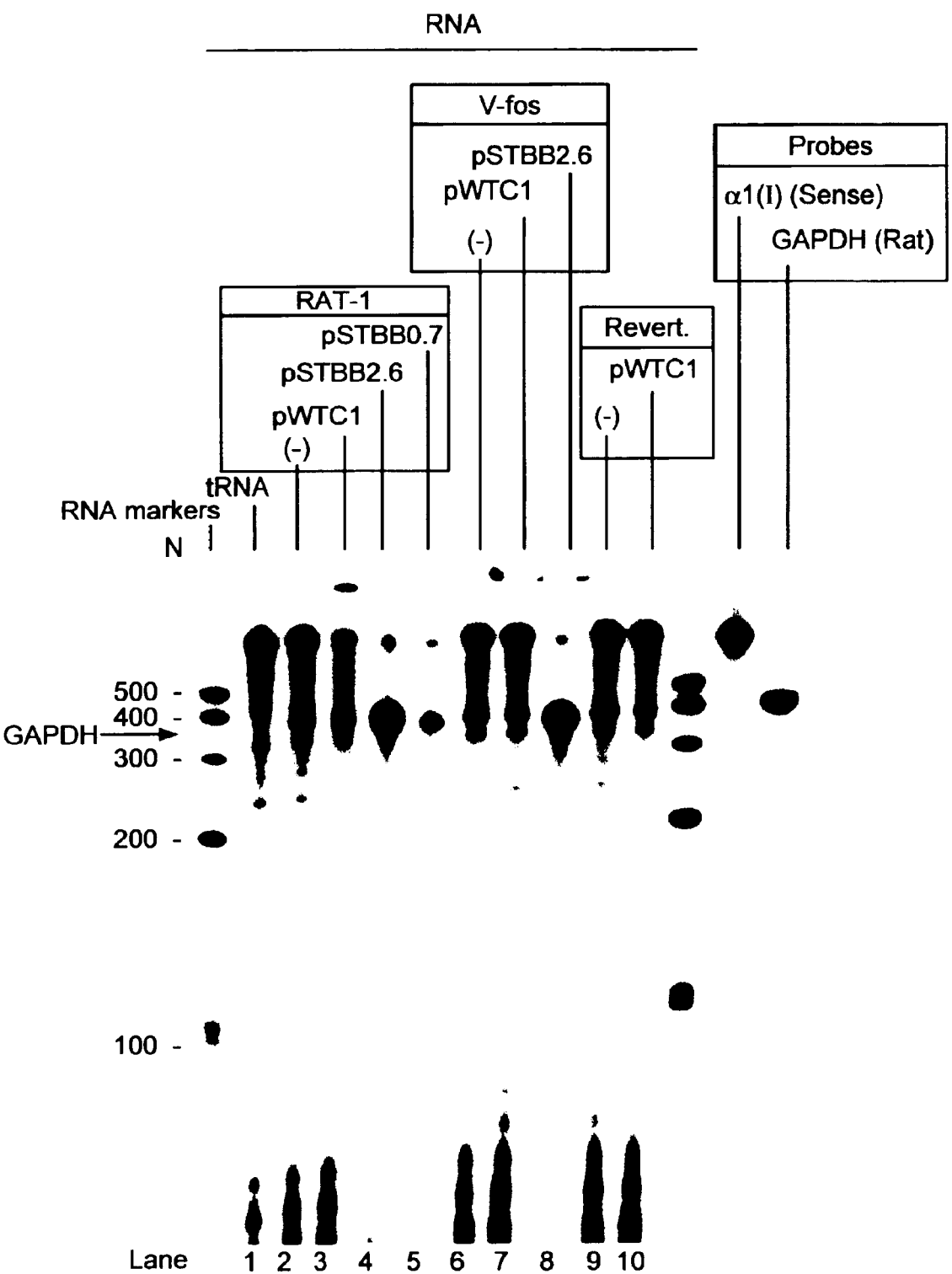
FIG. 7 shows an RNase T1 protection assay demonstrating the absence of antisense pro-α1(I) collagen mRNA in various rat fibroblast lines, either untransfected or transiently transfected by constructs carrying different lengths of the collagen gene. The GAPDH-rat antisense riboprobe and the expected protected band are as described in FIG. 3. The 850-nt α1(I) sense riboprobes transcribed in vitro by SP6 RNA polymerase from pSTBB0.7 were predicted to protect 5'-end α1(I) antisense transcripts of up to 585 nt. Evaluation of transfections by different plasmids is shown in FIG. 4C.

FIG. 7 shows the results of RNase T1 protection experiments using total RNA extracted from various rat fibroblast lines either untransfected, or transfected by one of constructs pWTC1, pSTBB2.6, and pSTBB0.7. The 850-nt sense riboprobes originate in the vector upstream of the position −221 bp of the rat α1(I) promoter and extend to +585 in the first intron. These probes could anneal to and protect any antisense RNA of up to 806 nt long in the 5'-end of the gene. The transfected cell lines would be expected to show increased intensity of this protected antisense RNA in comparison to control cells, if antisense RNA were present.

The significant amount of radioactive probe with increased mobility over that of the full length probe in FIG. 7 indicates that at least half of the probe was digested during the experiment. Since in this experiment, protection by antisense RNA would have been detected had protected product in fact been present, and as it was not detected, then in the cell lines of the present invention, the gene muting of α1(I) was not mediated by synthesis of antisense RNA.

Without being bound by any particular mechanism of the muting of gene expression, it is likely that both the rate of transcription and the post-transcriptional stability of the endogenous procollagen mRNA were decreased in the normal and v-fos transformed cells transfected with pWTC1. Further, in the revertant cell line, the endogenous procollagen gene which is partially liberated from the mechanisms of v-fos-induced suppression, was liberated also from the transgene-induced transcription muting, but not from pWTC1-induced post-transcriptional degradation. Data here show that the transcriptionally active 220 bp procollagen basal promoter construct, present in pColCAT0.2 and in promoter constructs of greater length, was transiently transfected into Rat-1 or v-fos transformed cells, and inhibited transcription of the endogenous collagen gene by at least 50%, presumably by competition for at least one transcription enhancing factor. However, introduction of the same transgenes into the revertant cells had no effect on the transcription rate (as determined by the steady-state level) of the endogenous collagen mRNA. Since pWTC1 transfection of the revertant cells reduced the steady-state level of the endogenous transcripts by 70%, the regulatory element(s) present at the 3' region of this gene (which are not present in the 5'-promoter constructs) can effect post-transcriptional muting of this gene. This mechanism could also explain the rapidity with which a low level steady-state mRNA was obtained in all cell lines analyzed herein following pWTC1-transfection.

To investigate whether differential antisense RNA synthesis plays a part in muting of the procollagen gene in rat fibroblast cell lines, the examples here analyzed RNA from transfected and untransfected cells by ribonuclease protection assays. No antisense RNA corresponding to the first five exons and four introns of the gene could be detected (FIG. 7).

Example 14

Muting by a Transgene can be Obtained Independent of Expression Level

In the Examples above, substantial muting in the absence of expression of the transgene supplied on exogenous nucleic acid was observed. In addition, substantial muting of an endogenous target gene may be obtained even in the presence of some transcription and translation of the transgene. With a transgene which is a gene fragment rather than an entire gene, the transgene can be transcribed, however as the resulting RNA product lacks a proper 3' terminus, the half-life of the RNA in a cell will be substantially reduced compared to that of a full length transcript. Further, the translation product is an incomplete peptide fragment translated from a 5' RNA fragment, which is physiologically unstable in vivo. The amount and stability of the peptide fragment can be further reduced by engineering translation stop codons (UAG, UAA and UGA) into the sequence in the correct reading frame.

These considerations indicate that in a method to obtain a muting gene fragment, a successful outcome can be achieved, and a muting nucleic acid can be obtained, even in the presence of some level of expression of the transgene. Once the muting nucleic acid is obtained, it can be further engineered by recombinant and nucleic acid synthetic methods to reduce the amount of expression of the transgene.

Example 15

Muting of Endogenous Genes Encoding an Unwanted Growth Factor, an Autoimmune Gene, or a Viral Gene The embodiments of the present invention include methods for muting one or more endogenous genes associated with various disease states, such as a gene encoding TNF-α, overexpression of which is associated with inflammation and wasting, a gene for an autoimmune-disease associated antibody, and a gene of a pathogenic organism such as the tat gene of a strain of human immunodeficiency virus, HIV.

The tat gene encodes a positive transacting regulatory 86 amino acid protein that is required for extension of HIV transcription initiated in the 5'-LTR promoter (U.S. Pat. No. 5,804,604; Daelemans, D. et al., Antivir. Chem. Chemother. 10:1–14 (1999)). This protein also regulates expression of genes encoding TNFα and TGFβ-1 in CNS cells (Sawaya, B. et al., J. Neuroimm. 87:33–42 (1998)). In the condition of integration in the genome of an infected cell, HIV-1 is transcriptionally silent. The transition to a stage of viral expression and replication requires tat expression and subsequent tat transactivation of other HIV genes. A nucleosome binding site, nuc-1, is positioned between −5 and +155 of this gene, and activation of HIV-infected T cells results in disruption of this nucleosome and increased HIV-1 transcription (Widlak, P. et al., Acta Biochim.Polon 45(1):209–219 (1998)).

Isolation of a nucleic acid capable of muting the tat gene is desirable for use in preventing intracellular HIV replication and maintenance of the HIV genome in a quiescent condition. Previous approaches to inhibition of HIV using a tat-inducible vector show that HIV infection is related to levels of expression of an exogenously provided gene encoding an inhibitor (Fraisier, C. et al., Gene Ther. 5: 1665–1676 (1998)). In contrast to this previous approach, muting of the tat gene as provided herein should not require expression of the exogenous transgene.

U.S. Pat. No. 5,837,512 shows vectors carrying various portions of the HIV genome, and vectors carrying portions with mutations at each of several sites. Muting DNA having HIV-1 genes or gene fragments that carry one or more binding sites for cellular transcription factors NF-κB and Sp1, or lacking each one or both of these sites, is provided to an infected cell by transformation of such nucleic acids on a non-integrating vector which is maintained in a transient non-integrated state. RNA from the treated and untreated cells is prepared, and the level of tat-specific RNA is measured by RNase protection using a probe having a sequence from the tat gene. Useful restriction sites for construction of these vectors and examples of these vectors are shown in U.S. Pat. No. 5,837,512, which is hereby incorporated by reference herein.

Isolation of the smallest effective length of the muting nucleic acid can be achieved by purification and subcloning of different fragments of HIV, starting from within the 5'-LTR (long terminal repeat having the promoter), and extending into the tat gene. Initially, large fragments (up to 2 kb) are tested for muting nucleic acid activity. Upon obtaining a positive muting response, the active portion can be isolated by subsequent restriction enzyme digestion, purification of fragments, cloning of each fragment into the vector, and testing each for having a muting activity.

TNFα regulates expression of several receptors in vascular endothelial cells (Giraudo, E. et al., J. Biol. Chem. 273:22128–35 (1998)) and TNF promoter polymorphisms affect transcriptional activation (Wilson, A. G., Proc. Natl. Acad. Sci. U.S. 94:3195–3199 (1997)). One polymorphism is associated with susceptibility to alcoholic steatohepatitis (Grove, J. et al., Hepatology 26:143–146 (1997)). Cell specific regulation of the human TNFα gene has been shown with cell transcription factors NFATp and AFT-2/JUN (Tsai, E. et al., Mol. Cell Biol. 16:5232–5244 (1996)).

Down regulation by expression of the TNFα gene has utility for a number of conditions, for example, it can activate transcription factor 2, which increases UVC-induced apoptosis of late-stage melanoma cells (Ivanov, V. et al., J. Biol. Chem. 274:14079–14089 (1999)). A muting nucleic acid for the endogenous TNFα gene can be provided by the methods herein, using a vector which is transiently maintained, the vector carrying each of a variety of 5'-fragments of this gene or the entire gene.

Muting nucleic acids can be provided to turn off expression of a gene encoding an immunoglobulin which is associated with an autoimmune disease. Autoimmune diseases include multiple sclerosis, systemic lupus erythematosus, and rheumatoid arthritis. Antibody molecules generally have a heterotetrameric quaternary structure, and include two copies of each of a heavy (H) chain and light (L) chain, so that any single antibody species is encoded by an H gene and an L gene. Substantial information is available on transcriptional regulation of expression of immunoglobin genes (Currie, R. A. Nucl. Acids Res. 18:2987–2992 (1990)): Lefrane, G. et al., Biochimie 72:7–17 (1990)); Staudt, L. et al., Ann. Rev. Immun. 9:373–398(1991)); and Wang, J. et al. Mol. Cell Bio. 11:75–83 (1991)).

To suppress expression of that molecule, a muting nucleic acid for the H gene or the L gene or both can be provided on a vector which is transiently maintained in the cell. Since antibody synthesis occurs primarily in leukocytes, for example in B cells, these cells can be isolated by methods known in the art from blood of a subject having an autoimmune disease (autoimmune cells), and the muting nucleic acid can be provided ex vivo. Alternatively, in vivo delivery of the muting nucleic acid can be achieved by use of methods that direct the nucleic acid to the leukocytes. The muting nucleic acid can be isolated from DNA fragments of upstream 5' portions of a gene encoding an H or an L chain, and extending into the gene. Further subcloning of the active portion can be achieved as described above.

TABLE 1

Specific Transient Expressions of Various Rodent pro-α1(1) collagen Promoter-CAT Constructs in Rat-1, v-fos Transformed 1302-4-1 and Revertant EMS-1-19 Cell Lines.

| | Promoter Activity[a] (pg CAT/plasmid copy number × $10^{-7}$) Cell Lines | | |
|---|---|---|---|
| Constructs | Rat-1 | v-fos transformants | Revertant |
| pColCAT3.5[b] | 0.7 ± 0.2 | ND[d] | ND[d] |
| pColCAT2.3[c] | 9.8 ± 0.5 | 1.7 ± 0.2 | 5.0 ± 0.3 |
| pColCAT0.9[b] | 4.7 ± 0.4 | 1.0 ± 0.2 | 2.3 ± 0.2 |
| pColCAT0.2[c] | 18.1 ± 2.5 | 3.2 ± 0.3 | 21.2 ± 3.6 |

[a]Data are obtained from the same samples used in FIG. 4. Transfected DNA and CAT enzyme determinations are described in Materials and Methods. Data are expressed as the mean of three determinations plus and minus the standard error of the mean.
[b]Rat promoter.
[c]Mouse promoter.
[d]ND: not detected.

sequence in the target gene, the nucleic acid composition being double stranded, wherein screening to identify comprises the steps of:
  (i) synthesizing a plurality of nucleic acid composition homologous to all or part of the target gene and introducing said plurality of nucleic acid composition into a cultured population of animal cells;
  (ii) selecting a nucleic acid composition that inhibits expression of the target gene in said cultured population of animal cells, thereby identifying said muting nucleic acid composition;
  (b) delivering the muting nucleic acid composition into a population of animal cells in vitro; and
  (c) muting expression of the target gene in said animal cells, wherein said muting nucleic acid composition inhibits expression of the target gene.

2. A method according to claim 1, wherein the target gene is selected from the group consisting of a collagen, tumor necrosis factor (TNF), tat, and an immunoglobulin gene.

3. A method according to claim 2, wherein the target gene is a collagen gene.

4. A method according to claim 3, wherein the target gene is pro-α1(I) collagen.

What is claimed is:

1. A method for muting expression of a target gene in a population of animal cells in vitro, the method comprising:
  (a) screening to identify a muting nucleic acid composition having a sequence that is homologous to a 5. A method according to claim 2, wherein the cultured population of animal cells is a population of mammalian cells.

* * * * *